United States Patent
Hillyard et al.

(10) Patent No.: US 6,893,826 B1
(45) Date of Patent: May 17, 2005

(54) COTTON EVENT PV-GHBK04 (757) AND COMPOSITIONS AND METHODS FOR DETECTION THEREOF

(75) Inventors: Jeanna R. Hillyard, St. Charles, MO (US); James K. Roberts, Chesterfield, MO (US); Minwei Ye, Framingham, MA (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 10/156,653

(22) Filed: May 28, 2002

Related U.S. Application Data

(63) Continuation of application No. 09/990,659, filed on Nov. 16, 2001, now abandoned.
(60) Provisional application No. 60/249,757, filed on Nov. 17, 2000.

(51) Int. Cl.[7] .......................... C12Q 1/68; C12P 19/34; C07H 21/04
(52) U.S. Cl. .................. 435/6; 435/91.2; 536/22.1; 536/24.3
(58) Field of Search .............. 435/6, 91.2; 536/22.1, 536/24.3

(56) References Cited

U.S. PATENT DOCUMENTS 5,500,365 A * 3/1996 Fischhoff et al. ............ 435/418
5,880,275 A   3/1999 Fischhoff et al.

FOREIGN PATENT DOCUMENTS

WO   WO 90/10076   9/1990

* cited by examiner

*Primary Examiner*—Kenneth R. Horlick
*Assistant Examiner*—Joyce Tung
(74) *Attorney, Agent, or Firm*—Timothy K. Ball, Esq.

(57) ABSTRACT

The present invention provides a cotton event PV-GHBK04 (757), a cotton plant that contains PV-GHBK04 (757) DNA molecules and its progeny thereof, and methods for producing cotton event PV-GHBK04 (757). The present invention also provides assays for detecting the presence of the 757 cotton event DNA sequences in a sample based on the DNA sequence of the recombinant construct inserted into the cotton genome and of genomic sequences flanking the insertion site, and provides amplicons and sequences which are diagnostic for the presence of event 757 nucleic acids in a sample.

6 Claims, 4 Drawing Sheets

SEQUENCE LISTING

<160> NUMBER OF SEQ ID NOS: 21

<210> SEQ ID NO 1
<211> LENGTH: 20
<212> TYPE: DNA
<213> ORGANISM: artificial sequence
<220> FEATURE:
<223> OTHER INFORMATION: a diagnostic nucleotide sequence that spans the
      link between the genome and the insert at 5' end.
<220> FEATURE:

```
<221> NAME/KEY: misc_feature
<222> LOCATION: (1)..(20)
<223> OTHER INFORMATION: a 5' genome-insert junction nucleotide sequence
      which is/is complementary to a sequence diagnostic for nucleic
      acids derived from the cotton event 757 recombinant genome.

<400> SEQUENCE: 1
gtttgcttgg acactgatag                                                20

<210> SEQ ID NO 2
<211> LENGTH: 20
<212> TYPE: DNA
<213> ORGANISM: artificial sequence
<220> FEATURE:
<223> OTHER INFORMATION: a diagnostic nucleotide sequence that spans the
      link between the genome and the insert at 3' end.
<220> FEATURE:
<221> NAME/KEY: misc_feature
<222> LOCATION: (1)..(20)
<223> OTHER INFORMATION: a 3' genome-insert junction nucleotide sequence
      which is/is complementary to a sequence diagnostic for nucleic
      acids derived from the cotton event 757 recombinant genome.

<400> SEQUENCE: 2
aaaccctttc tggaaaaata                                                20

<210> SEQ ID NO 3
<211> LENGTH: 20
<212> TYPE: DNA
<213> ORGANISM: Gossypium hirsutum
<220> FEATURE:
<221> NAME/KEY: misc_feature
<222> LOCATION: (1)..(20)
<223> OTHER INFORMATION:

<400> SEQUENCE: 3
tgttctgtgg aaaaggaagg                                                20

<210> SEQ ID NO 4
<211> LENGTH: 20
<212> TYPE: DNA
<213> ORGANISM: Gossypium hirsutum
<220> FEATURE:
<221> NAME/KEY: misc_feature
<222> LOCATION: (1)..(20)
<223> OTHER INFORMATION:

<400> SEQUENCE: 4
atgcctgcag gtcaattcaa                                                20

<210> SEQ ID NO 5
<211> LENGTH: 138
<212> TYPE: DNA
<213> ORGANISM: artificial sequence
<220> FEATURE:
<223> OTHER INFORMATION: a non-naturally occurring, partial 5' CrylAc
      nucleotide sequence.
<220> FEATURE:
<221> NAME/KEY: misc_feature
<222> LOCATION: (1)..(138)
<223> OTHER INFORMATION: part of a 5' non-functional sequence inserted
      into the cotton genome in cotton event 757.

<400> SEQUENCE: 5
acactgatag tttaaactga aggcgggaaa cgacaatctg atcccagctt gcatgcctgc    60
aggtcaattc aatattgtgg caggacattg ctacatgata cctcttagaa ttgtttagac   120
ttcagatcga tcttgtca                                                 138
```

<210> SEQ ID NO 6
<211> LENGTH: 767
<212> TYPE: DNA
<213> ORGANISM: Gossypium hirsutum
<220> FEATURE:
<221> NAME/KEY: Unsure
<222> LOCATION: (1)..(767)
<223> OTHER INFORMATION: 5' cotton (Gossypium hirsutum) genome sequence

<400> SEQUENCE: 6

```
gtcccggggg cttatcctgt attcatttgc acccacataa acagccaaat taaccaaacc      60
catattcaac tgaaactccc aaagccattc ctactttagc ttttcaccca ctaactcaaa     120
agaaaacact cacctagctt ctttgctttt tcttttggat tgttttagat ctacaaaaag     180
atgattcaag aactccttgg aggttcttct tgcttaaact ttggagggga gaggaagatc     240
tccatcaatg gaagcatttt ggaaggaacc cccacttctt ctccatcacc atcatcttct     300
tcttcttcgg cgacgacttc atcgaccact aattcatcga atccggagaa tcatcaccag     360
aatttgaggt gccccaggtg tgattcctcc aacacaaagt tctgctatta caacaactac     420
aacctcactc agcctcgtca cttttgcaag acttgccgtc ggtattggac caaggagga     480
gctctcagaa acgttcctat tggtggtggg tgtaggaaaa acaaaagcac tactggtgtt     540
tcaacatctc tggggaaatc aacttcttcc aagatgaaaa cagtagtttc tgaaattgga     600
agatctgggt tcgatcatga gcttcagtct actccaattc tttggacttc agcggcccag     660
acttcccatc ttctatccaa tctaacctca atgagagcta ccctaaaccc taaccctaac     720
acattgtcta accctgttag tattaaggaa gaagtgagtt tgcttgg                   767
```

<210> SEQ ID NO 7
<211> LENGTH: 206
<212> TYPE: DNA
<213> ORGANISM: artificial sequence
<220> FEATURE:
<223> OTHER INFORMATION: a non-naturally occurring, partial 3' Cry1Ac
      nucleotide sequence.
<220> FEATURE:
<221> NAME/KEY: misc_feature
<222> LOCATION: (1)..(206)
<223> OTHER INFORMATION: part of arbitrarily assigned 3' end DNA sequence inserted into the cotton event 757 genome.

<400> SEQUENCE: 7

```
tgagggatca agccacagca gcccactcga ccttctagcc gacccagacg agccaaggga     60
tctttttgga atgctgctcc gtcgtcaggc tttccgacgt ttgggtggtt gaacagaagt    120
cattatcgca cggaatgcca agcactcccg aggggaaccc tgtggttggc atgcacatac    180
aaatggacga acggataaac cctttc                                         206
```

<210> SEQ ID NO 8
<211> LENGTH: 307
<212> TYPE: DNA
<213> ORGANISM: Gossypium hirsutum
<220> FEATURE:
<221> NAME/KEY: Unsure
<222> LOCATION: (1)..(307)
<223> OTHER INFORMATION: 3' cotton (Gossypium hirsutum) genome sequence

<400> SEQUENCE: 8

```
tggaaaaata atcaacacca cgctcaacaa caacagaata ataatgggtt ccttgtaggt     60
gaagttcaaa acacaggtat tcaagaactg tatcaaaggc tcaaatcatc atcaagttat    120
tactctgata cttcagcagt aattctaagc aatgtcgctt cttcttcatc aacatccatt    180
```

-continued

```
ttggagtcag ctccagttgc tgggggagaa ttgggttact ggaatccggc attttcatca    240
tcgtggtctg atcttccaac aactaatggt gcatatcctt aaaataaccc tttacctttc    300
gtttaat                                                              307
```

```
<210> SEQ ID NO 9
<211> LENGTH: 26
<212> TYPE: DNA
<213> ORGANISM: artificial sequence
<220> FEATURE:
<223> OTHER INFORMATION: a PCR primer oligonucleotide sequence
      complementary to 5' cotton genome sequence.
<220> FEATURE:
<221> NAME/KEY: misc_feature
<222> LOCATION: (1)..(26)
<223> OTHER INFORMATION: 5' cotton (Gossypium hirsutum) genome PCR
      primer

<400> SEQUENCE: 9
gagagagata ggcactaaag taagca                                         26
```

```
<210> SEQ ID NO 10
<211> LENGTH: 28
<212> TYPE: DNA
<213> ORGANISM: artificial sequence
<220> FEATURE:
<223> OTHER INFORMATION: a PCR primer oligonucleotide sequence
      complementary to 5' insert sequence.
<220> FEATURE:
<221> NAME/KEY: misc_feature
<222> LOCATION: (1)..(28)
<223> OTHER INFORMATION: 5' insert PCR primer

<400> SEQUENCE: 10
ttagacaaat tgtcacggtc taccagaa                                       28
```

```
<210> SEQ ID NO 11
<211> LENGTH: 24
<212> TYPE: DNA
<213> ORGANISM: artificial sequence
<220> FEATURE:
<223> OTHER INFORMATION: a PCR primer oligonucleotide sequence
      complementary to 3' insert sequence.
<220> FEATURE:
<221> NAME/KEY: misc_feature
<222> LOCATION: (1)..(24)
<223> OTHER INFORMATION: 3' insert PCR primer

<400> SEQUENCE: 11
ttcccaacga tcaaggcgag ttac                                           24
```

```
<210> SEQ ID NO 12
<211> LENGTH: 27
<212> TYPE: DNA
<213> ORGANISM: artificial sequence
<220> FEATURE:
<223> OTHER INFORMATION: a PCR primer oligonucleotide sequence
      complementary to 3' cotton genome sequence.
<220> FEATURE:
<221> NAME/KEY: misc_feature
<222> LOCATION: (1)..(27)
<223> OTHER INFORMATION: 3' cotton (Gossypium hirsutum) genome PCR
      primer

<400> SEQUENCE: 12
ttgatgcact tacgaaagaa gaaccga                                        27
```

```
<210> SEQ ID NO 13
```

<211> LENGTH: 905
<212> TYPE: DNA
<213> ORGANISM: artificial sequence
<220> FEATURE:
<223> OTHER INFORMATION: a 5' cotton genome + insert sequence.
<220> FEATURE:
<221> NAME/KEY: misc_feature
<222> LOCATION: (1)..(905)
<223> OTHER INFORMATION: 5' cotton (Gossypium hirsutum) genome + insert
    sequence

<400> SEQUENCE: 13

```
gtcccggggg cttatcctgt attcatttgc acccacataa acagccaaat taaccaaacc      60
catattcaac tgaaactccc aaagccattc ctactttagc ttttcaccca ctaactcaaa     120
agaaaacact cacctagctt ctttgctttt tcttttggat tgttttagat ctacaaaaag     180
atgattcaag aactccttgg aggttcttct tgcttaaact ttggaggggga gaggaagatc    240 tccatcaatg gaagcatttt ggaaggaacc cccacttctt ctccatcacc atcatcttct    300
tcttcttcgg cgacgacttc atcgaccact aattcatcga atccggagaa tcatcaccag    360
aatttgaggt gccccaggtg tgattcctcc aacacaaagt tctgctatta caacaactac    420
aacctcactc agcctcgtca cttttgcaag acttgccgtc ggtattggac caaaggagga    480
gctctcagaa acgttcctat tggtggtggg tgtaggaaaa acaaaagcac tactggtgtt    540
tcaacatctc tggggaaatc aacttcttcc aagatgaaaa cagtagtttc tgaaattgga    600 agatctggt tcgatcatga gcttcagtct actccaattc tttggacttc agcggcccag     660
acttcccatc ttctatccaa tctaacctca atgagagcta ccctaaaccc taaccctaac    720
acattgtcta accctgttag tattaaggaa gaagtgagtt tgcttggaca ctgatagttt    780
aaactgaagg cgggaaacga caatctgatc ccagcttgca tgcctgcagg tcaattcaat    840
attgtggcag gacattgcta catgatacct cttagaattg tttagacttc agatcgatct    900
tgtca                                                                 905
```

<210> SEQ ID NO 14
<211> LENGTH: 513
<212> TYPE: DNA
<213> ORGANISM: artificial sequence
<220> FEATURE:
<223> OTHER INFORMATION: a 3' cotton genome + insert sequence.
<220> FEATURE:
<221> NAME/KEY: misc_feature
<222> LOCATION: (1)..(513)
<223> OTHER INFORMATION: 3' cotton (Gossypium hirsutum) genome + insert
    sequence

<400> SEQUENCE: 14

```
tgagggatca agccacagca gcccactcga ccttctagcc gacccagacg agccaaggga      60 tcttttttgga atgctgctcc gtcgtcaggc tttccgacgt ttgggtggtt gaacagaagt    120
cattatcgca cggaatgcca agcactcccg aggggaaccc tgtggttggc atgcacatac    180
aaatggacga acggataaac cctttctgga aaaataatca acaccacgct caacaacaac    240
agaataataa tgggttcctt gtaggtgaag ttcaaaacac aggtattcaa gaactgtatc    300
aaaggctcaa atcatcatca agttattact ctgatacttc agcagtaatt ctaagcaatg    360
tcgcttcttc ttcatcaaca tccatttttgg agtcagctcc agttgctggg ggagaattgg    420
gttactggaa tccggcattt tcatcatcgt ggtctgatct tccaacaact aatggtgcat    480
atccttaaaa taaccctttta cctttcgttt aat                                 513
```

-continued

```
<210> SEQ ID NO 15
<211> LENGTH: 4973
<212> TYPE: DNA
<213> ORGANISM: artificial sequence
<220> FEATURE:
<223> OTHER INFORMATION: part of the cotton genome flanking the 5' end
      of the arbitrarily assigned 5' end of the inserted sequence.
<220> FEATURE:
<221> NAME/KEY: misc_feature
<222> LOCATION: (1)..(4973)
<223> OTHER INFORMATION: sequence of 5' flank to full-length cry1Ac
      coding region

<400> SEQUENCE: 15
cggcccagac ttcccatctt ctatccaatc taacctcaat gagagctacc ctaaaccta       60 accctaacac attgtctaac cctgttagta ttaaggaaga agtgagtttg cttggacact     120
gatagtttaa actgaaggcg ggaaacgaca atctgatccc agcttgcatg cctgcaggtc     180
aattcaatat tgtggcagga cattgctaca tgatacctct tagaattgtt tagacttcag     240
atcgatcttg tcagtctgaa agacccaaaa acaaatgcaa tttcttttct ggtagaccgt     300
gacaatttgt ctaagatgta tctgatttaa tgccttttgt atataataca ctcatctaat     360
ctagttaatt tagcttcaga gtaaattact tcagcatatt tatacgtgcc aagtgccaac     420
catatcaaat tagctaagca gacagttgaa gtacacaaaa caaaagcatc atatgctgat     480
ttatttattc atagatggag ctcaagtcat agttaaatag cccgatactt tcctcgctca     540
ctatgagcta ttacagcata cattttagta ctacatactt attcagtaaa aagccctcaa     600
aattgaagac aaaggacggg atccccgggt accgagctcg aattcaggcc tctagatctc     660
attattcctc catcaagaga agctccacgc tgtccacgat gaaggttccc tcggtttcac     720
cgatctcgat ccacactttg tcggtctcag gaaagtactc aagctccttg gtaacatagc     780
caactggaag tggtgtgtag tccctgtaac ctctgttgaa ctcgcaaggg ttctcacgtc     840
tgccatctgt gtaggatttc tcctcgtaca cggaggcata gtcagcagga acggaaggag     900
cttcgttgta acctctgtta cggctagtgt aggcacctcc gtactcttcc tgattcacag     960
tgtagtcgtt gcaagtaacg tgttgttgg atagatttc ttcctcgacg cagttggaga     1020
acttaagctc gtcggtgttg ttctcgatct cgtggatggt cacgcaaccc tcaccgtatc     1080
cctccttgta agcggtcaca cggagaatgt agcctctacc tggacagact ctaacctctt     1140
gggacacttc agcttcccac tcaggcacaa ccaggacgga acgctgattg ttctgttcct     1200
ccacgtccac atgaccttc acattccagc agctgaggcc attgttgaag tcaccgttct     1260
tgatgacgtt tctggcatcg tacaaggaga atgcggtaaa gatacgtccc tcaagttcct     1320
cgaagatggc agcgttcaca ccagggatca cggacaactc aggcaagtaa gcctcacgaa     1380
tgctgtgcac acgtttgtct gcggcgtgga tcatggcgat gttggtgtcg gcttgcaact     1440
gatcatattg ggagttcacg aacaaagcat ccacggactc tttggcctcc ttgtaaacga     1500
tgttagtttc ccattcgagt ttctcacgtt tgtccctcca cttcttctct gctctcttca     1560
cacgagcgag agcttcaccg accaatggtt tctcttcgag aaactcaagg ttgccaagtc     1620
ttgcgtgtcc gtcttgggtc ttgatcttga agatgaccca gactccgagg tcctcattca     1680
ggtcagtaca tccacatcg atgtccaagg agaagtgatg agaatggtgg gcacacttct     1740
cgccatccct gcaggagcag tccaagtcag gattccactc aaggtgtgga gcgcatctgt     1800
taggctctcc acacttccca atgggagatt gggcagaaag tggccagagg gaaccagtac     1860
ctgggacatt cacggtctcg tgcttggcat tgtacctgat cgagtagatt tcaaggtctt     1920
```

-continued

```
ggctgtcttc gatgtagcct ctaagttgat acctggtgaa ggctttgagt ttggactcat    1980
cgatcttctg gtacaagtag gtagggtagc actcgtcgaa agttccggag agggtgacgt    2040
agttctcctt gaacacatcg tcgcctcctt ggatggtgat cccggtgctt ccaccccaac    2100
cacgttctgg ctgcctgttg atgtctttga agttggagtc ttgcaagaga ttcctctcgt    2160
cgctgagacg cttggcgtgt ttaacttfct cggagagttc acgcttctcg tcgaggcaga    2220
actcatcgct aaggtaggtg accaagttgg acacttggtc aatgtgatag tcagtaacgt    2280
tagttttcaa gccaagctga ttggtggagg taaagagggc gttcacagcc ttctgggctc    2340
tctcaaggtt gtactcagcc tcgagtgttg cagtaactgg aatgaactcg aatctgtcga    2400
taatcactcc tgcagtccca ctaaagtttc taacacccac gatgttaccg agtgaagatg    2460
taaaagcatt ggcactttca aagtaaccga atcgctgga ttggagatta tccaaggagg    2520
tagctgtagc tggaactgta ttggagaaga tggatgaatt accccaatta acgttgaggt    2580
gaatagggc cacagaagca tacctcacac gaactctata tctggtagat gtggatggga    2640
agtgaattgg aacttcaata taccctctat tctgaatgtt atttccactg ctgttgagtc    2700
taacgaggtc tccaccagtg aatcctggtc ctgaaatgac agaaccgttg aagagaaagt    2760
ttcccttcac tgcagggatt tgagtaatac tatcggatgc gatgatgttg ttgaactcag    2820
cactacgatg tatccaagag aacataggag ctctgatgat gctcacggaa ctgttgctga    2880
atccggaacg gaacatggac acgtggctca acctgtggga gaatccttgc ctgggtggca    2940
cattgttgtt ctgtggaaaa ggaaggtggc tcctacaaat gccatcattg cgataaagga    3000
aaggccatcg ttgaagatgc ctctgccgac agtggtccca aagatggacc cccacccacg    3060
aggagcatcg tggaaaaaga agacgttcca accacgtctt caaagcaagt ggattgatgt    3120
gatatctcca ctgacgtaag ggatgacgca caatcccact atccttcgca agacccttcc    3180
tctatataag gaagttcatt tcatttggag aggacacgct gacaagctga ctctagcaga    3240
tctccatgga caacaaccca aacatcaacg aatgcattcc atacaactgc ttgagtaacc    3300
cagaagttga agtacttggt ggagaacgca ttgaaaccgg ttacactccc atcgacatct    3360
ccttgtcctt gacacagttt ctgctcagcg agttcgtgcc aggtgctggg ttcgttctcg    3420
gactagttga catcatctgg ggtatctttg gtccatctca atgggatgca ttcctggtgc    3480
aaattgagca gttgatcaac cagaggatcg aagagttcgc caggaaccag gccatctcta    3540
ggttggaagg attgagcaat ctctaccaaa tctatgcaga gagcttcaga gagtgggaag    3600
ccgatcctac taacccagct ctccgcgagg aaatgcgtat tcaattcaac gacatgaaca    3660
gcgccttgac cacagctatc ccattgttcg cagtccagaa ctaccaagtt cctctcttgt    3720
ccgtgtacgt tcaagcagct aatcttcacc tcagcgtgct tcgagacgtt agcgtgtttg    3780
ggcaaaggtg gggattcgat gctgcaacca tcaatagccg ttacaacgac cttactaggc    3840
tgattggaaa ctacaccgac cacgctgttc gttggtacaa cactggcttg gagcgtgtct    3900
ggggtcctga ttctagagat tggattagat acaaccagtt caggagagaa ttgaccctca    3960
cagttttgga cattgtgtct ctcttcccga actatgactc cagaacctac cctatccgta    4020
cagtgtccca acttaccaga gaaatctata ctaacccagt tcttgagaac ttcgacggta    4080
gcttccgtgg ttctgcccaa ggtatcgaag ctccatcag gagcccacac ttgatggaca    4140
tcttgaacag cataactatc tacaccgatg ctcacagagg agagtattac tggtctggac    4200
accagatcat ggcctctcca gttggattca gcgggcccga gtttaccttt cctctctatg    4260
gaactatggg aaacgccgct ccacaacaac gtatcgttgc tcaactaggt cagggtgtct    4320
```

```
acagaacaaa cactgatagt ttaaactgaa ggcgggaaac gacaatctga tcccagcttg    4380
catgcctgca ggtcaattca atattgtggc aggacattgc tacatgatac ctcttagaat    4440
tgtttagact tcagatcgat cttgtcagtc tgaaagaccc aaaaacaaat gcaatttctt    4500
ttctggtaga ccgtgacaat ttgtctaaga tgtatctgat ttaatgcctt ttgtatataa    4560
tacactcatc taatctagtt aatttagctt cagagtaaat tacttcagca tatttatacg    4620
tgccaagtgc caaccatatc aaattagcta agcagacagt tgaagtacac aaaacaaaag    4680
catcatatgc tgatttattt attcatagat ggagctcaag tcatagttaa atagcccgat    4740
actttcctcg ctcactatga gctattacag catacatttt agtactacat acttattcag    4800
taaaaagccc tcaaaattga agacaaagga cgggatcccc gggtaccgag ctcgaattca    4860
ggcctctaga tctcattatt cctccatcaa gagaagctcc acgctgtcca cgatgaaggt    4920
tccctcggtt tcaccgatct cgatccacac tttgtcggtc tcaggaaagt act           4973
```

<210> SEQ ID NO 16
<211> LENGTH: 19
<212> TYPE: DNA
<213> ORGANISM: artificial sequence
<220> FEATURE:
<223> OTHER INFORMATION: a 5' primer nucleotide sequence.
<220> FEATURE:
<221> NAME/KEY: misc_feature
<222> LOCATION: (1)..(19)
<223> OTHER INFORMATION: 5' primer to 5' flanking sequence of SEQ ID NO:
      15 from 8 to 26;

<400> SEQUENCE: 16
gacttcccat cttctatcc                                                    19

<210> SEQ ID NO 17
<211> LENGTH: 19
<212> TYPE: DNA
<213> ORGANISM: artificial sequence
<220> FEATURE:
<223> OTHER INFORMATION: a 3' primer nucleotide sequence.
<220> FEATURE:
<221> NAME/KEY: misc_feature
<222> LOCATION: (1)..(19)
<223> OTHER INFORMATION: 3'primer to partial e35S promoter of SEQ ID NO:
      15 from 3154 to 3136;

<400> SEQUENCE: 17
attgtgcgtc atcccttac                                                    19

<210> SEQ ID NO 18
<211> LENGTH: 22
<212> TYPE: DNA
<213> ORGANISM: artificial sequence
<220> FEATURE:
<223> OTHER INFORMATION: a 5' primer nucleotide sequence.
<220> FEATURE:
<221> NAME/KEY: misc_feature
<222> LOCATION: (1)..(22)
<223> OTHER INFORMATION: 5'primer to partial 3' cry1Ac sequence of
      SEQ ID NO: 15 from 2581 to 2603;

<400> SEQUENCE: 18 gaatagggt cacagaagca ta                                                 22

<210> SEQ ID NO 19
<211> LENGTH: 20
<212> TYPE: DNA
<213> ORGANISM: artificial sequence

```
<220> FEATURE:
<223> OTHER INFORMATION: a 3' primer nucleotide sequence.
<220> FEATURE:
<221> NAME/KEY: misc_feature
<222> LOCATION: (1)..(20)
<223> OTHER INFORMATION: 3'primer to partial 5' cry1Ac sequence of
      SEQ ID NO: 15 from 3455 to 3435;

<400> SEQUENCE: 19
ggaccaaaga taccccagat                                               20

<210> SEQ ID NO 20
<211> LENGTH: 19
<212> TYPE: DNA
<213> ORGANISM: artificial sequence
<220> FEATURE:
<223> OTHER INFORMATION: a 5' primer nucleotide sequence.
<220> FEATURE:
<221> NAME/KEY: misc_feature
<222> LOCATION: (1)..(19)
<223> OTHER INFORMATION: 5'primer to partial e35S promoter of SEQ ID NO:
      15 from 2993 to 3011;

<400> SEQUENCE: 20
ataaaggaaa ggccatcgt                                                19

<210> SEQ ID NO 21
<211> LENGTH: 25
<212> TYPE: DNA
<213> ORGANISM: artificial sequence
<220> FEATURE:
<223> OTHER INFORMATION: a 3' primer nucleotide sequence.
<220> FEATURE:
<221> NAME/KEY: misc_feature
<222> LOCATION: (1)..(25)
<223> OTHER INFORMATION: 3'primer to full-length cry1Ac sequence of
      SEQ ID NO: 15 from 4973 to 4949;

<400> SEQUENCE: 21
agtactttcc tgagaccgac aaagt                                         25
```

US 6,893,826 B1

COTTON EVENT PV-GHBK04 (757) AND COMPOSITIONS AND METHODS FOR DETECTION THEREOF

CROSS REFERENCE TO RELATED APPLICATIONS

This application is a continuation of U.S. application Ser. No. 09/990,659, filed Nov. 16, 2001 now abandon which claims the benefit of priority to U.S. Provisional Application Ser. No. 60/249,757, filed on Nov. 17, 2000.

FIELD OF THE INVENTION

The present invention relates to the field of plant molecular biology, more specifically the invention relates to identification of nucleic acids from the transgenic cotton event 757. Most specifically, the invention relates to a *Lepidoptera* resistant cotton (*Gossypium hirsutum*) plant event 757 and its progeny thereof, to methods for producing the *Lepidoptera* resistant cotton plant event 757, and to assays for detecting the presence of cotton event 757 in a sample and compositions thereof.

BACKGROUND OF THE INVENTION

Cotton is an important fiber crop in many areas of the world. The methods of biotechnology have been applied to cotton for improvement of the agronomic traits and the quality of the product. The method of introducing transgenes into cotton plants is demonstrated in U.S. Pat. No. 5,004, 863. One such agronomic trait important in cotton production is resistance to *Lepidoptera* insect damage. This trait has been introduced into cotton plants and is a successful product now used in cotton production. The expression of foreign genes in plants is known to be influenced by their chromosomal position, perhaps due to chromatin structure (e.g., heterochromatin) or the proximity of transcriptional regulation elements (e.g., enhancers) close to the integration site (Weising et al., Ann. Rev. Genet 22:421–477, 1988). For this reason, it is often necessary to screen a large number of events in order to identify an event characterized by optimal expression of an introduced gene of interest. For example, it has been observed in plants and in other organisms that there may be a wide variation in levels of expression of one or more exogenously introduced genes among events. There may also be differences in spatial or temporal patterns of expression, for example, differences in the relative expression of a transgene in various plant tissues, that may not correspond to the patterns expected from transcriptional regulatory elements present in the introduced gene construct. For this reason, it is common to produce hundreds to thousands of different events and screen those events for a single event that exhibits the desired transgene expression levels and patterns for commercial purposes. An event that exhibits such desired levels or patterns of transgene expression is useful for introgressing the transgene into other genetic backgrounds by sexual outcrossing using conventional breeding methods. Progeny of such crosses maintain the transgene expression characteristics of the original transformant. This strategy is used to ensure reliable gene expression in a number of varieties that are well adapted to local growing conditions.

It would be advantageous to be able to detect the presence of a particular event in order to determine whether progeny of a sexual cross contain a transgene of interest. In addition, a method for detecting a particular event would be helpful for complying with regulations requiring the pre-market approval and labeling of foods derived from recombinant crop plants, for example. It is possible to detect the presence of a transgene by any well known nucleic acid detection method such as nucleic acid amplification techniques or nucleic acid hybridization using nucleic acid probes. These detection methods generally focus on frequently used genetic elements, such as promoters, terminators, marker genes, etc. As a result, such methods may not be useful for discriminating between different events, particularly those produced using the same, similar, or substantially related nucleic acid constructs unless the sequence of chromosomal DNA adjacent to the inserted DNA ("flanking DNA") is known. An event-specific thermal amplification assay is discussed, for example, by Windels et al. (Med. Fac. Landbouww, Univ. Gent 64/5b: 459–462, 1999), who identified glyphosate tolerant soybean event 40-3-2 using a primer set spanning the junction between the inserted heterologous DNA and flanking chromosomal DNA, specifically one primer that included sequence from the insert and a second primer that included sequence from flanking DNA, to produce an amplicon which proved to be diagnostic for the event.

SUMMARY OF THE INVENTION

According to an aspect of the invention, there is provided a novel cotton (*Gossypium hirsutum*) plant designated PV-GHBK04 or cotton event 757. This invention relates to the seeds and to the progeny of cotton event 757, and to methods for detecting nucleic acids contained within and produced by the event 757 in a biological or commercial sample.

According to another aspect of the invention, methods of producing a *Lepidoptera* resistant cotton plant are provided that comprise the steps of: (a) sexually crossing a first parental cotton line comprising cotton event 757 DNA that exhibits a trait which confers resistance to one or more *Lepidoptera* insect species upon the event, and a second parental cotton line that does not exhibit a trait conferring *Lepidoptera* insect resistance to said second cotton line, thereby producing a plurality of progeny plants; and (b) selecting a progeny plant that exhibits resistance to one or more *Lepidoptera* insect species. The methods are useful for introgressing the *Lepidoptera* resistance trait into different genetic backgrounds. Such methods may optionally comprise a further step of back-crossing the progeny plant to the second parental cotton line to produce a cotton plant that is also *Lepidoptera* resistant.

According to still another aspect of the invention, compositions and methods are provided for detecting the presence of the transgene/genomic insertion region from a cotton plant designated as cotton event 757. DNA sequences are provided that comprise at least one junction sequence of event 757 identified as SEQ ID NO: 1 and SEQ ID NO: 2, and complements thereof; wherein a junction sequence spans the junction between a heterologous DNA sequence inserted into the genome and the cotton genome DNA sequence flanking the insertion site, and is diagnostic for the event.

According to yet another aspect of the invention, compositions and methods are provided for detecting the presence of the novel nucleic acid sequences within the inserted transgene identified as SEQ ID NO: 3 and SEQ ID NO: 4, and complements thereof.

According to yet another aspect of the invention, the DNA sequences that comprise at least 11 or more contiguous nucleotides of the DNA sequence of SEQ ID NO: 5, a similar length of the DNA sequence of SEQ ID NO: 6, a similar length of the DNA sequence of SEQ ID NO: 7, and a similar length of SEQ ID NO: 8 for use as primers in nucleic acid amplification methods, and as probes. The amplicons produced using particular pairs of these primers are diagnostic for cotton event 757.

The amplicons produced by DNA primers homologous or complementary to SEQ ID NO: 9 and SEQ ID NO: 10 and using event 757 DNA as template are an aspect of the invention. The amplicons produced by DNA primers homologous or complementary to SEQ ID NO: 11 and SEQ ID NO: 12 and using event 757 DNA as template are another aspect of the invention.

According to yet another aspect of the invention, methods of detecting the presence of DNA corresponding to the cotton event 757 event in a commercial or biological sample are provided. Such methods comprise the steps of: (a) contacting the sample comprising DNA with a primer set that, when used in a nucleic acid amplification reaction with DNA from cotton event 757, produces an amplicon that is diagnostic for cotton event 757; (b) performing a nucleic acid amplification reaction, thereby producing the amplicon; and (c) detecting the amplicon.

According to yet still another aspect of the invention, methods of detecting the presence of a DNA corresponding to the 757 event in a sample, such methods comprising the steps of: (a) contacting the sample comprising DNA with a probe that hybridizes under stringent hybridization conditions with DNA from cotton event 757 and does not hybridize under the stringent hybridization conditions with a control cotton plant which is a cotton plant other than a cotton event 757; (b) subjecting the sample and probe to stringent hybridization conditions; and (c) detecting hybridization of the probe to the DNA.

The foregoing and other aspects of the invention will become more apparent from the following detailed description and accompanying sequence listings.

BRIEF DESCRIPTION OF THE SEQUENCES

Figure 1:
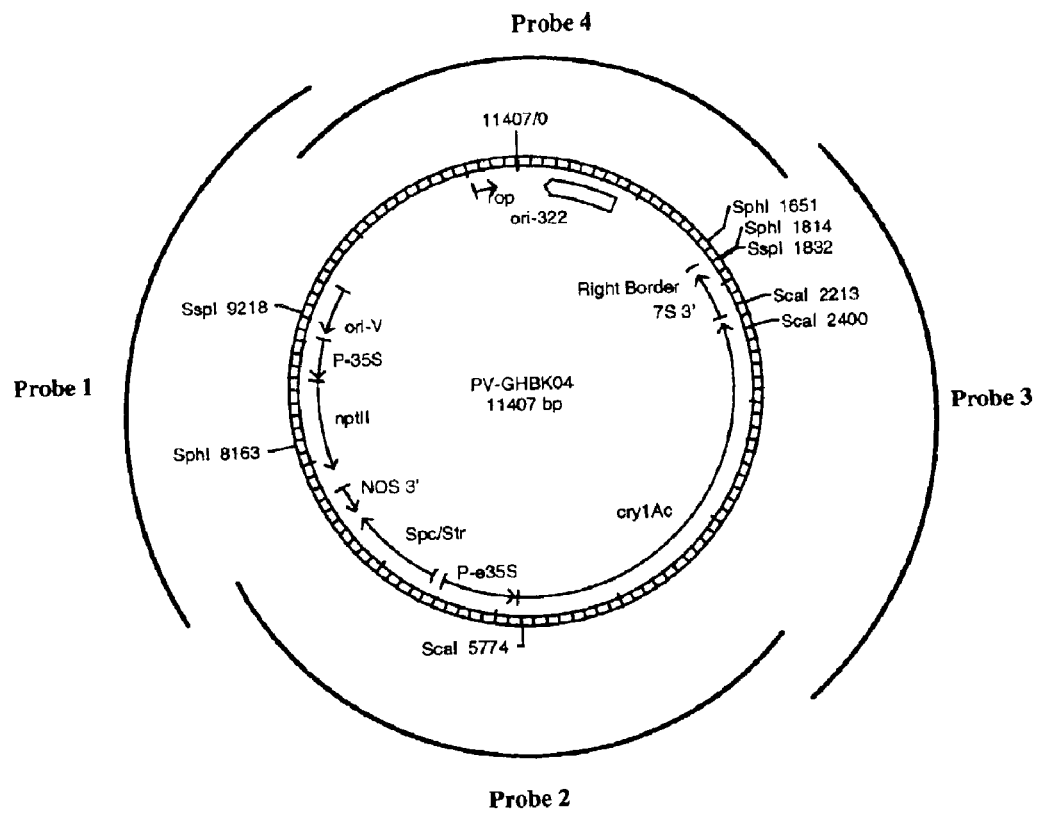
FIG. 1 illustrates a circular map of plasmid PV-GHBK04 that was used to generate the cotton event 757, and further illustrates the approximate positions of sequences of the plasmid that are used herein as probes.
Figure 2:
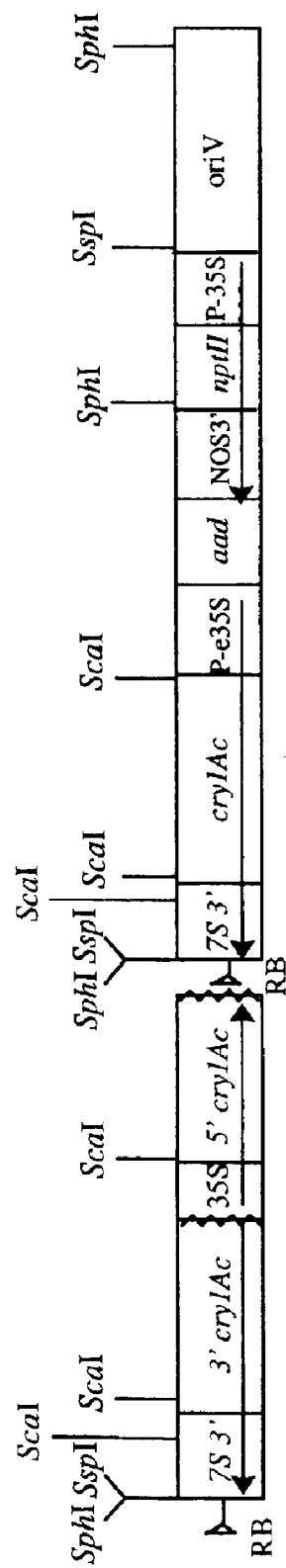
FIG. 2 illustrates a linear map depicting a schematic representation of the inserted heterologous DNA in cotton event 757. The diagram represents the architecture of the inserted heterologous DNA present in cotton event 757. The arbitrarily assigned 5' end of the inserted heterologous DNA is depicted towards the left of the linear map, and the arbitrarily assigned 3' end of the inserted heterologous DNA is depicted towards the right of the linear map. The primary and functional insert is depicted from about the center of the linear map and extends toward the right of the linear map through the indicated P-35S segment.

SEQ ID NO: 1 (5-TTTGCTTGGACACTGATAG 3') discloses a nucleotide sequence which is or is complementary to a sequence which is diagnostic for nucleic acids derived from the cotton event 757 recombinant genome, comprising, at the 5' end of SEQ ID NO: 1, the first ten nucleotides of cotton genomic DNA sequence (from nucleotide position 1 through position 10) followed by the arbitrarily assigned 5'end of the non-functional cotton event 757 inserted DNA sequence, which is linked to the first ten nucleotides of the inserted DNA sequence (from nucleotide position 11 through position 20). Sequences comprising at least eleven (11) consecutive nucleotides selected from the group of nucleotides comprising SEQ ID NO: 1 and which also contain the dinucleotide at position 10 and 11 of SEQ ID NO: 1 and complements thereof are diagnostic for the cotton event 757 DNA sequences in a sample.

SEQ ID NO: 2 (5'AAACCCTTTCTGGAAAAATA3') discloses a nucleotide sequence which is or is complementary to a sequence which is diagnostic for nucleic acids derived from the cotton event 757 recombinant genome, comprising, at the 5 end of SEQ ID NO: 2, the terminal ten nucleotides of an arbitrarily assigned 3'end of a non-functional cotton event 757 inserted sequence (nucleotides from position 1 through position 10) being linked at the 3'end to the linear sequence of the first ten nucleotides of cotton genomic DNA sequence immediately adjacent to and flanking the arbitrarily assigned 3'end of the non-functional cotton event 757 inserted sequence (nucleotides from position 11 through position 20). Sequences comprising at least eleven (11) consecutive nucleotides selected from the group of nucleotides comprising SEQ ID NO: 2 and which also contain the dinucleotide at position 10 and 11 of SEQ ID NO: 2 and complements thereof are diagnostic for the cotton event 757 DNA sequences in a sample.

SEQ ID NO: 3 (5TGTTCTGTGGAAAAGGAAGG 3') discloses a nucleotide sequence which is or is complementary to a sequence which is diagnostic for nucleic acids derived from the cotton event 757 recombinant genome. Sequences comprising at least eleven (11) consecutive nucleotides selected from the group of nucleotides comprising SEQ ID NO: 3 and which also contain the dinucleotide at position 10 and 11 of SEQ ID NO: 3 and complements thereof are diagnostic for the cotton event 757 DNA sequences in a sample.

SEQ ID NO: 4 (5'ATGCCTGCAGGTCAATTCAA3') discloses a nucleotide sequence which is or is complementary to a sequence which is diagnostic for nucleic acids derived from the cotton event 757 recombinant genome. Sequences comprising at least eleven (11) consecutive nucleotides selected from the group of nucleotides comprising SEQ ID NO: 4 and which also contain the dinucleotide at position 10 and 11 of SEQ ID NO: 4 and complements thereof are diagnostic for the cotton event 757 DNA sequences in a sample.

SEQ ID NO: 5 (5'ACACTGATAGTTTAAACTGAA GGCGGGAAACGACAATCTGATCCCAGCTTGC ATGCCTGCAGGTCAATTCAATATTGTGGCAGGACAT TGCTACATGATACCTCTTAGAATTGTTTAGACTTCA GATCGATCTTG TCA3') discloses a part of a non-functional sequence inserted into the cotton genome in cotton event 757. The 5'terminal ten nucleotides from position 1 to 10 correspond to nucleotides as set forth in SEQ ID NO: 1 from nucleotide position 11 to 20.

```
SEQ ID NO: 6 5'cotton genome sequence (5'GTCCCGGGGG CTTATCCTGT

ATTCATTTGC ACCCACATAA ACAGCCAAAT TAACCAAACC CATATTCAAC TGAAACTCCC

AAAGCCATTC CTACTTTAGC TTTTCACCCA CTAACTCAAA AGAAAACACT CACCTAGCTT

CTTTGCTTTT TCTTTTGGAT TGTTTTAGAT CTACAAAAAG ATGATTCAAG AACTCCTTGG

AGGTTCTTCT TGCTTAAACT TTGGAGGGGA GAGGAAGATC TCCATCAATG GAAGCATTTT

GGAAGGAACC CCCACTTCTT CTCCATCACC ATCATCTTCT TCTTCTTCGG CGACGACTTC

ATCGACCACT AATTCATCGA ATCCGGAGAA TCATCACCAG AATTTGAGGT GCCCCAGGTG

TGATTCCTCC AACACAAAGT TCTGCTATTA CAACAACTAC AACCTCACTC AGCCTCGTCA

CTTTTGCAAG ACTTGCCGTC GGTATTGGAC CAAAGGAGGA GCTCTCAGAA ACGTTCCTAT

TGGTGGTGGG TGTAGGAAAA ACAAAAGCAC TACTGGTGTT TCAACATCTC TGGGGAAATC

AACTTCTTCC AAGATGAAAA CAGTAGTTTC TGAAATTGGA AGATCTGGGT TCGATCATGA

GCTTCAGTCT ACTCCAATTC TTTGGACTTC AGCGGCCCAG ACTTCCCATC TTCTATCCAA

TCTAACCTCA ATGAGAGCTA CCCTAAACCC TAACCCTAAC ACATTGTCTA ACCCTGTTAG

TATTAAGGAA GAAGTGAGTT TGCTTGG3')
``` discloses the 5' proximal first 767 base pair cotton genomic DNA sequence flanking the arbitrarily assigned 5' end of the inserted sequence in the cotton event 767 genome. Nucleotides from position 758 through 767 correspond to nucleotides 1 through 10 as set forth in SEQ ID NO: 1.

```
SEQ ID NO: 8

(5'TGGAAAAATA ATCAACACCA CGCTCAACAA CAACAGAATA

ATAATGGGTT CCTTGTAGGT GAAGTTCAAA ACACAGGTAT TCAAGAACTG TATCAAAGGC

TCAAATCATC ATCAAGTTAT TACTCTGATA CTTCAGCAGT AATTCTAAGC AATGTCGCTT

CTTCTTCATC AACATCCATT TTGGAGTCAG CTCCAGTTGC TGGGGGAGAA TTGGGTTACT

GGAATCCGGC ATTTTCATCA TCGTGGTCTG ATCTTCCAAC AACTAATGGT GCATATCCTT

AAAATAACCC TTTACCTTTC GTTTAAT3'
``` discloses a part of the arbitrarily assigned 3' end DNA sequence inserted into the cotton event 757 genome. Nucleotides from position 197 through 206 correspond to nucleotides from position 1 through 10 as set forth in SEQ ID NO: 2.

SEQ ID NO: 7

(5'TGAGGGATCA AGCCACAGCA GCCCACTCGA CCTTCTAGCC

GACCCAGACG AGCCAAGGGA TCTTTTTGGA ATGCTGCTCC GTCGTCAGGC TTTCCGACGT

TTGGGTGGTT GAACAGAAGT CATTATCGCA CGGAATGCCA AGCACTCCCG AGGGGAACCC

TGTGGTTGGC ATGCACATAC AAATGGACCA ACGGATAAAC CCTTTC3')

discloses the 3' proximal first 307 cotton event 757 genomic nucleotides flanking the arbitrarily assigned 3' end of the DNA inserted into the genome in event 757. Nucleotides from position 1 through position 10 correspond to nucleotides 11 through 20 as set forth in SEQ ID NO: 2.

SEQ ID NO: 9 (5'GAGAGAGATAGGCACTA AAGTAAGCA3') corresponds to Primer G as described herein, and represents a sequence which is or is complementary to a sequence within the cotton genome flanking the arbitrarily assigned 5' end of the inserted DNA in cotton event 757. SEQ ID NO: 9 and SEQ ID NO: 10 represent a primer pair for use in producing an amplicon comprising about 1032 base pairs which is diagnostic for cotton event 757.

SEQ ID NO: 10 (5 TTAGACAAATTGTCACGGT CTACCAGAA3') corresponds to Primer H as described herein, and represents a sequence which is or is complementary to a sequence within the inserted sequence as set forth in SEQ ID NO: 15 from nucleotide position 287 through nucleotide position 314. SEQ ID NO: 9 and SEQ ID NO: 10 represent a primer pair for use in producing an amplicon comprising about 1032 base pairs which is diagnostic for cotton event 757.

SEQ ID NO: 11 (5TTCCCAACGATCAAG GCGAGTTAC3) corresponds to Primer I as described herein, and represents a sequence which is or is complementary to a sequence within the arbitrarily assigned 3' end of the inserted DNA sequence in cotton event 757, and can be used as a part of a primer pair along with SEQ ID NO: 12 to produce an amplicon comprising about 682 base pairs which is diagnostic for cotton event 757.

SEQ ID NO: 12 (5TTGATGCACT TACGAAAGAA GAACCGA3') corresponds to Primer J as described herein, and represents a sequence which is or is complementary to a sequence within 3' end flanking DNA sequence within the cotton genome 3' to the arbitrarily assigned 3' end of the inserted DNA sequence in event 757. SEQ ID NO: 12 can be used as a part of a primer pair along with SEQ ID NO: 11 to produce an amplicon comprising about 682 base pairs which is diagnostic for cotton event 757.

SEQ ID NO: 13

(5'GTCCCGGGGG CTTATCCTGT ATTCATTTGC ACCCACATAA

ACAGCCAAAT TAACCAAACC CATATTCAAC TGAAACTCCC AAAGCCATTC CTACTTTAGC

TTTTCACCCA CTAACTCAAA AGAAAACACT CACCTAGCTT CTTTGCTTTT TCTTTTGGAT

TGTTTTAGAT CTACAAAAAG ATGATTCAAG AACTCCTTGG AGGTTCTTCT TGCTTAAACT

TTGGAGGGGA GAGGAAGATC TCCATCAATG GAAGCATTTT GGAAGGAACC CCCACTTCTT

CTCCATCACC ATCATCTTCT TCTTCTTCGG CGACGACTTC ATCGACCACT AATTCATCGA

ATCCGGAGAA TCATCACCAG AATTTGAGGT GCCCCAGGTG TGATTCCTCC AACACAAAGT

TCTGCTATTA CAACAACTAC AACCTCACTC AGCCTCGTCA CTTTTGCAAG ACTTGCCGTC

GGTATTGGAC CAAAGGAGGA GCTCTCAGAA ACGTTCCTAT TGGTGGTGGG TGTAGGAAAA

ACAAAAGCAC TACTGGTGTT TCAACATCTC TGGGGAAATC AACTTCTTCC AAGATGAAAA

CAGTAGTTTC TGAAATTGGA AGATCTGGGT TCGATCATGA GCTTCAGTCT ACTCCAATTC

TTTGGACTTC AGCGGCCCAG ACTTCCCATC TTCTATCCAA TCTAACCTCA ATGAGAGCTA

CCCTAAACCC TAACCCTAAC ACATTGTCTA ACCCTGTTAG TATTAAGGAA GAAGTGAGTT

TGCTTGGACA CTGATAGTTT AAACTGAAGG CGGGAAACGA CAATCTGATC CCAGCTTGCA

TGCCTGCAGG TCAATTCAAT ATTGTGGCAG GACATTGCTA CATGATACCT CTTAGAATTG

TTTAGACTTC AGATCGATCT TGTCA3' corresponds to the 5 cotton genome sequence (nucleotide position 1 through nucleotide position 767) linked to the arbitrarily assigned 5' end of the inserted DNA sequence (nucleotide position 768 through nucleotide position 905).

SEQ ID NO: 14

(5' TGAGGGATCA AGCCACAGCA GCCCACTCGA CCTTCTAGCC

GACCCAGACG AGCCAAGGGA TCTTTTTGGA ATGCTGCTCC GTCGTCAGGC TTTCCGACGT

TTGGGTGGTT GAACAGAAGT CATTATCGCA CGGAATGCCA AGCACTCCCG AGGGGAACCC

TGTGGTTGGC ATGCACATAC AAATGGACGA ACGGATAAAC CCTTTCTGGA AAAATAATCA

ACACCACGCT CAACAACAAC AGAATAATAA TGGGTTCCTT GTAGGTGAAG TTCAAAACAC

AGGTATTCAA GAACTGTATC AAAGGCTCAA ATCATCATCA AGTTATTACT CTGATACTTC

AGCAGTAATT CTAAGCAATG TCGCTTCTTC TTCATCAACA TCCATTTTGG AGTCAGCTCC

AGTTGCTGGG GGAGAATTGG GTTACTGGAA TCCGGCATTT TCATCATCGT GGTCTGATCT

TCCAACAACT AATGGTGCAT ATCCTTAAAA TAACCCTTTA CCTTTCGTTT AAT 3' corresponds to a part of the sequence of the arbitrarily assigned 3' end of the inserted sequence (nucleotide position 1 through 206) linked to the 3' end cotton genomic DNA flanking sequence 3' of the inserted sequence (nucleotide position 207 through 513).

SEQ ID NO: 15

(5'CGGCCCAGAC TTCCCATCTT CTATCCAATC TAACCTCAAT

GAGAGCTACC CTAAACCCTA ACCCTAACAC ATTGTCTAAC CCTGTTAGTA TTAAGGAAGA

AGTGAGTTTG CTTGGACACT GATAGTTTAA ACTGAAGGCG GGAAACGACA ATCTGATCCC

AGCTTGCATG CCTGCAGGTC AATTCAATAT TGTGGCAGGA CATTGCTACA TGATACCTCT

TAGAATTGTT TAGACTTCAG ATCGATCTTG TCAGTCTGAA AGACCCAAAA ACAAATGCAA

TTTCTTTTCT GGTAGACCGT GACAATTTGT CTAAGATGTA TCTGATTTAA TGCCTTTTGT

ATATAATACA CTCATCTAAT CTAGTTAATT TAGCTTCAGA GTAAATTACT TCAGCATATT

TATACGTGCC AAGTGCCAAC CATATCAAAT TAGCTAAGCA GACAGTTGAA GTACACAAAA

CAAAAGCATC ATATGCTGAT TTATTTATTC ATAGATGGAG CTCAAGTCAT AGTTAAATAG

CCCGATACTT TCCTCGCTCA CTATGAGCTA TTACAGCATA CATTTTAGTA CTACATACTT

ATTCAGTAAA AAGCCCTCAA AATTGAAGAC AAAGGACGGG ATCCCCGGGT ACCGAGCTCG

AATTCAGGCC TCTAGATCTC ATTATTCCTC CATCAAGAGA AGCTCCACGC TGTCCACGAT

GAAGGTTCCC TCGGTTTCAC CGATCTCGAT CCACACTTTG TCGGTCTCAG GAAAGTACTC

AAGCTCCTTG GTAACATAGC CAACTGGAAG TGGTGTGTAG TCCCTGTAAC CTCTGTTGAA

CTCGCAAGGG TTCTCACGTC TGCCATCTGT GTAGGATTTC TCCTCGTACA CGGAGGCATA

GTCAGCAGGA ACGGAAGGAG CTTCGTTGTA ACCTCTGTTA CGGCTAGTGT AGGCACCTCC

GTACTCTTCC TGATTCACAG TGTAGTCGTT GCAAGTAACG GTGTTGTTGG GATAGATTTC

TTCCTCGACG CAGTTGGAGA ACTTAAGCTC GTCGGTGTTG TTCTCGATCT CGTGGATGGT

CACGCAACCC TCACCGTATC CCTCCTTGTA AGCGGTCACA CGGAGAATGT AGCCTCTACC

TGGACAGACT CTAACCTCTT GGGACACTTC AGCTTCCCAC TCAGGCACAA CCAGGACGGA

ACGCTGATTG TTCTGTTCCT CCACGTCCAC ATGACCTTTC ACATTCCAGC AGCTGAGGCC

ATTGTTGAAG TCACCGTTCT TGATGACGTT TCTGGCATCG TACAAGGAGA ATGCGGTAAA

GATACGTCCC TCAAGTTCCT CGAAGATGGC AGCGTTCACA CCAGGGATCA CGGACAACTC

AGGCAAGTAA GCCTCACGAA TGCTGTGCAC ACGTTTGTCT GCGGCGTGGA TCATGGCGAT

-continued

```
GTTGGTGTCG GCTTGCAACT GATCATATTG GGAGTTCACG AACAAAGCAT CCACGGACTC

TTTGGCCTCC TTGTAAACGA TGTTAGTTTC CCATTCGAGT TTCTCACGTT TGTCCCTCCA

CTTCTTCTCT GCTCTCTTCA CACGAGCGAG AGCTTCACCG ACCAATGGTT TCTCTTCGAG

AAACTCAAGG TTGCCAAGTC TTGCGTGTCC GTCTTGGGTC TTGATCTTGA AGATGACCCA

GACTCCGAGG TCCTCATTCA GGTCAGTACA TCCCACATCG ATGTCCAAGG AGAAGTGATG

AGAATGGTGG GCACACTTCT CGCCATCCCT GCAGGAGCAG TCCAAGTCAG GATTCCACTC

AAGGTGTGGA GCGCATCTGT TAGGCTCTCC ACACTTCCCA ATGGGAGATT GGGCAGAAAG

TGGCCAGAGG GAACCAGTAC CTGGGACATT CACGGTCTCG TGCTTGGCAT TGTACCTGAT

CGAGTAGATT TCAAGGTCTT GGCTGTCTTC GATGTAGCCT CTAAGTTGAT ACCTGGTGAA

GGCTTTGAGT TTGGACTCAT CGATCTTCTG GTACAAGTAG GTAGGGTAGC ACTCGTCGAA

AGTTCCGGAG AGGGTGACGT AGTTCTCCTT GAACACATCG TCGCCTCCTT GGATGGTGAT

CCCGGTGCTT CCACCCCAAC CACGTTCTGG CTGCCTGTTG ATGTCTTTGA AGTTGGAGTC

TTGCAAGAGA TTCCTCTCGT CGCTGAGACG CTTGGCGTGT TTAACTTTCT CGGAGAGTTC

ACGCTTCTCG TCGAGGCAGA ACTCATCGCT AAGGTAGGTG ACCAAGTTGG ACACTTGGTC

AATGTGATAG TCAGTAACGT TAGTTTTCAA GCCAAGCTGA TTGGTGGAGG TAAAGAGGGC

GTTCACAGCC TTCTGGGCTC TCTCAAGGTT GTACTCAGCC TCGAGTGTTG CAGTAACTGG

AATGAACTCG AATCTGTCGA TAATCACTCC TGCAGTCCCA CTAAAGTTTC TAACACCCAC

GATGTTACCG AGTGAAGATG TAAAAGCATT GGCACTTTCA AAGTAACCGA AATCGCTGGA

TTGGAGATTA TCCAAGGAGG TAGCTGTAGC TGGAACTGTA TTGGAGAAGA TGGATGAATT

ACCCCAATTA ACGTTGAGGT GAATAGGGGT CACAGAAGCA TACCTCACAC GAACTCTATA

TCTGGTAGAT GTGGATGGGA AGTGAATTGG AACTTCAATA TACCCTCTAT TCTGAATGTT

ATTTCCACTG CTGTTGAGTC TAACGAGGTC TCCACCAGTG AATCCTGGTC CTGAAATGAC

AGAACCGTTG AAGAGAAAGT TTCCCTTCAC TGCAGGGATT TGAGTAATAC TATCGGATGC

GATGATGTTG TTGAACTCAG CACTACGATG TATCCAAGAG AACATAGGAG CTCTGATGAT

GCTCACGGAA CTGTTGCTGA ATCCGGAACG GAACATGGAC ACGTGGCTCA ACCTGTGGGA

GAATCCTTGC CTGGGTGGCA CATTGTTGTT CTGTGGAAAA GGAAGGTGGC TCCTACAAAT

GCCATCATTG CGATAAAGGA AAGGCCATCG TTGAAGATGC CTCTGCCGAC AGTGGTCCCA

AAGATGGACC CCCACCCACG AGGAGCATCG TGGAAAAAGA AGACGTTCCA ACCACGTCTT

CAAAGCAAGT GGATTGATGT GATATCTCCA CTGACGTAAG GGATGACGCA CAATCCCACT

ATCCTTCGCA AGACCCTTCC TCTATATAAG GAAGTTCATT TCATTTGGAG AGGACACGCT

GACAAGCTGA CTCTAGCAGA TCTCCATGGA CAACAACCCA AACATCAACG AATGCATTCC

ATACAACTGC TTGAGTAACC CAGAAGTTGA AGTACTTGGT GGAGAACGCA TTGAAACCGG

TTACACTCCC ATCGACATCT CCTTGTCCTT GACACAGTTT CTGCTCAGCG AGTTCGTGCC

AGGTGCTGGG TTCGTTCTCG GACTAGTTGA CATCATCTGG GGTATCTTTG GTCCATCTCA

ATGGGATGCA TTCCTGGTGC AAATTGAGCA GTTGATCAAC CAGAGGATCG AAGAGTTCGC

CAGGAACCAG GCCATCTCTA GGTTGGAAGG ATTGAGCAAT CTCTACCAAA TCTATGCAGA

GAGCTTCAGA GAGTGGGAAG CCGATCCTAC TAACCCAGCT CTCCGCGAGG AAATGCGTAT

TCAATTCAAC GACATGAACA GCGCCTTGAC CACAGCTATC CCATTGTTCG CAGTCCAGAA

CTACCAAGTT CCTCTCTTGT CCGTGTACGT TCAAGCAGCT AATCTTCACC TCAGCGTGCT

TCGAGACGTT AGCGTGTTTG GGCAAAGGTG GGGATTCGAT GCTGCAACCA TCAATAGCCG
```

-continued

```
TTACAACGAC CTTACTAGGC TGATTGGAAA CTACACCGAC CACGCTGTTC GTTGGTACAA

CACTGGCTTG GAGCGTGTCT GGGGTCCTGA TTCTAGAGAT TGGATTAGAT ACAACCAGTT

CAGGAGAGAA TTGACCCTCA CAGTTTTGGA CATTGTGTCT CTCTTCCCGA ACTATGACTC

CAGAACCTAC CCTATCCGTA CAGTGTCCCA ACTTACCAGA GAAATCTATA CTAACCCAGT

TCTTGAGAAC TTCGACGGTA GCTTCCGTGG TTCTGCCCAA GGTATCGAAG GCTCCATCAG

GAGCCCACAC TTGATGGACA TCTTGAACAG CATAACTATC TACACCGATG CTCACAGAGG

AGAGTATTAC TGGTCTGGAC ACCAGATCAT GGCCTCTCCA GTTGGATTCA GCGGGCCCGA

GTTTACCTTT CCTCTCTATG GAACTATGGG AAACGCCGCT CCACAACAAC GTATCGTTGC

TCAACTAGGT CAGGGTGTCT ACAGAACAAA CACTGATAGT TTAAACTGAA GGCGGGAAAC

GACAATCTGA TCCCAGCTTG CATGCCTGCA GGTCAATTCA ATATTGTGGC AGGACATTGC

TACATGATAC CTCTTAGAAT TGTTTAGACT TCAGATCGAT CTTGTCAGTC TGAAAGACCC

AAAAACAAAT GCAATTTCTT TTCTGGTAGA CCGTGACAAT TTGTCTAAGA TGTATCTGAT

TTAATGCCTT TTGTATATAA

TACACTCATC TAATCTAGTT AATTTAGCTT CAGAGTAAAT TACTTCAGCA TATTTATACG

TGCCAAGTGC CAACCATATC AAATTAGCTA AGCAGACAGT TGAAGTACAC AAAACAAAAG

CATCATATGC TGATTTATTT ATTCATAGAT GGAGCTCAAG TCATAGTTAA ATAGCCCGAT

ACTTTCCTCG CTCACTATGA GCTATTACAG CATACATTTT AGTACTACAT ACTTATTCAG

TAAAAAGCCC TCAAAATTGA AGACAAAGGA CGGGATCCCC GGGTACCGAG CTCGAATTCA

GGCCTCTAGA TCTCATTATT CCTCCATCAA GAGAAGCTCC ACGCTGTCCA CGATGAAGGT

TCCCTCGGTT TCACCGATCT CGATCCACAC TTTGTCGGTC TCAGGAAAGT ACT3'
``` corresponds to the consensus sequence for a part of the cotton genome flanking the 5'end of the arbitrarily assigned 5' end of the inserted sequence in cotton event 757, the nucleotide sequence from position 1 through position 114 corresponding to the cotton genome sequence flanking the 5' end of the inserted sequence; an *Agrobacterium tumefaciens* right border sequence corresponding to nucleotide positions 116 through 170; a 7S transcriptional termination sequence corresponding to nucleotide positions 171 through 619; a partial Cry1Ac coding sequence corresponding to nucleotide positions 620 through 2596; a partial e35S promoter sequence corresponding to nucleotide sequence positions 2957 through 3213; a partial Cry1Ac coding sequence corresponding to nucleotide positions 3214 through 4326; an *Agrobacterium tumefaciens* right border sequence corresponding to nucleotide positions 4327 through 4391; a 7S transcriptional termination sequence corresponding to nucleotide sequence positions 4392 through 4832; and a part of the functional insertion sequence encoding a part of a Cry1Ac protein corresponding to nucleotide positions 4833 through 4971.

SEQ ID NO: 16 (5GACTTCCCATCTTCTATCC3) corresponds to Primer A as described herein, an oligonucleotide sequence which is or is complementary to a sequence within the cotton genomic DNA sequence flanking the 5'end of the inserted DNA from nucleotide position 8 through position 26 as set forth in SEQ ID NO: 15. When paired in an amplification reaction with SEQ ID NO: 17 and template in a sample containing nucleic acid sequences derived from cotton event 757, produces an amplicon of about 3150 base pairs which is diagnostic for event 757.

SEQ ID NO: 17 (5'ATTGTGCGTCATCCCTTAC3) corresponds to Primer B as described herein, an oligonucleotide sequence which is or is complementary to a sequence within the arbitrarily assigned 5'end of the inserted DNA in cotton event 757 from nucleotide position 3154 through position 3136 as set forth in SEQ ID NO: 15. When paired in an amplification reaction with SEQ ID NO: 16 and template in a sample containing nucleic acid sequences derived from cotton event 757, produces an amplicon of about 3150 base pairs which is diagnostic for event 757.

SEQ ID NO: 18 (5'GAATAGGGGTCACAGAAGCATA3) corresponds to Primer C as described herein, an oligonucleotide sequence which is or is complementary to a sequence within the arbitrarily assigned 5'end of the inserted DNA in cotton event 757 from nucleotide position 2581 through position 2502 as set forth in SEQ ID NO: 15. When paired in an amplification reaction with SEQ ID NO: 19 and template in a sample containing nucleic acid sequences derived from cotton event 757, produces an amplicon of about 874 base pairs which is diagnostic for event 757.

SEQ ID NO; 19 (5'GGACCAAAGATACCCCAGAT3) corresponds to Primer D as described herein, an oligonucleotide sequence which is or is complementary to a sequence within the arbitrarily assigned 5'end of the inserted DNA in cotton event 757 from nucleotide position 3435 through position 3454 as set forth in SEQ ID NO: 15. When paired in an amplification reaction with SEQ ID NO: 18 and template in a sample containing nucleic acid sequences derived from cotton event 757, produces an amplicon of about 874 base pairs which is diagnostic for event 757.

SEQ ID NO: 20 (5'ATAAAGGAAAGGCCATCGT3) corresponds to Primer E as described herein, an oligonucleotide sequence which is or is complementary to a sequence within the arbitrarily assigned 5'end of the inserted DNA in cotton event 757 from nucleotide position 2993 through position 3011 as set forth in SEQ ID NO: 15. When paired in an amplification reaction with SEQ ID NO: 21 and template in a sample containing nucleic acid sequences derived from cotton event 757, produces an amplicon of about 1979 base pairs which is diagnostic for event 757.

SEQ ID NO: 21 (5'AGTACTTTCCTGAGACCGACAAAGT3) corresponds to Primer F as described herein, an oligonucleotide sequence which is or is complementary to a sequence within a part of the carboxyl terminal Cry1A coding sequence within the functional inserted DNA within cotton event 757 from nucleotide position 4949 through position 4973 as set forth in SEQ ID NO: 15. When paired in an amplification reaction with SEQ ID NO: 20 and template in a sample containing nucleic acid sequences derived from cotton event 757, produces an amplicon of about 1979 base pairs which is diagnostic for event 757.

DETAILED DESCRIPTION OF THE PREFERRED EMBODIMENTS

The following definitions and methods are provided to better define the present invention and to guide those of ordinary skill in the art in the practice of the present invention. Unless otherwise noted, terms are to be understood according to conventional usage by those of ordinary skill in the relevant art. Definitions of common terms in molecular biology may also be found in Rieger et al., *Glossary of Genetics: Classical ard Molecular*, 5th edition, Springer-Verlag: New York, 1991; and Lewin, *Genes V*, Oxford University Press: New York, 1994. The nomenclature for DNA bases as set forth at 37 CFR § 1.822 is used.

As used herein, the term "cotton" means *Gossypium hirsutum* and includes all plant varieties that can be bred with cotton, including wild cotton species.

As used herein, the term "comprising" means "including but not limited to".

As used herein, "expression" refers to the transcription and stable accumulation of sense (mRNA) or antisense RNA derived from the nucleic acid of the invention. Expression may also refer to translation of mRNA into a polypeptide.

A transgenic "event" is a recombinantly derived plant produced by the incorporation of heterologous DNA into the genome of a plant cell. The term "heterologous DNA" is meant to include a nucleic acid construct that includes a transgene of interest. Plant cells that have had heterologous DNA incorporated into the plant cells' genome are said to have been transformed. Plants are then regenerated from the transformed plant cells, and so a population of plants is obtained resulting from the insertion of the transgene into the genome of the progenitor transformed plant cell. Various criteria are then used to screen the transformed plants, for example, such as the appearance of the leaves, the ability to produce flowers and seeds in a typically normal manner, and the level of expression of the transgene. Plants which are selected as candidates for commercialization are subsequently characterized to determine the relative position within the genome of the insertion heterologous DNA. The term "event" refers to the original transformed cell and progeny of the transformed cell that include the heterologous DNA inserted into the cell genome, including daughter plant cells, plants produced from the original plant cell, and seeds and tissues produced from the plants produced from the original plant cell, so long as the plant, plant cell, seed, or plant tissue contains the heterologous DNA inserted into the genome. The term "event" also refers to progeny produced by a sexual outcross between the plant produced from the transformed cell and another variety that include the heterologous DNA. Even after repeated back-crossing to a recurrent parent, the inserted transgene DNA and flanking genomic DNA (genomic/transgene DNA) from the transformed parent is present in the progeny of the cross at the same chromosomal location. The term "event" also refers to DNA from the original transformant comprising the inserted DNA and flanking genomic sequence immediately adjacent to the inserted DNA that would be expected to be transferred to a progeny that receives inserted DNA including the transgene of interest as the result of a sexual cross of one parental line that includes the inserted DNA (e.g., the original transformed cell and progeny resulting from selfing) and a parental line that does not contain the inserted DNA.

It is also to be understood that two different transgenic plants can also be mated to produce offspring that contain two independently segregating added, exogenous genes. Selfing of appropriate progeny can produce plants that are homozygous for both added, exogenous genes. Backcrossing to a parental plant and out-crossing with a non-transgenic plant are also contemplated, as is vegetative propagation. Descriptions of other breeding methods that are commonly used for different traits and crops can be found in one of several references, e.g., Fehr, in *Breeding Methods for Cultivar Development*, Wilcox J. ed., American Society of Agronomy, Madison Wis. (1987). Backcross breeding has been used to transfer genes for a simply inherited, highly heritable trait into a desirable homozygous cultivar, inbred line, or elite germplasm which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting parent is expected to have the attributes of the recurrent parent (e.g., cultivar) and the desirable trait transferred from the donor parent.

A "probe" is an isolated nucleic acid to which is attached a conventional detectable label or reporter molecule, e.g., a radioactive isotope, ligand, chemiluminescent agent, or enzyme. Such a probe is complementary to a strand of a target nucleic acid, in the case of the present invention, to a strand of genomic DNA from cotton event 757 whether from a cotton plant or from a sample that includes DNA from the event. Probes according to the present invention include not only deoxyribonucleic or ribonucleic acids but also polyamides and other probe materials that bind specifically to a target DNA sequence and can be used to detect the presence of that target DNA sequence.

"Primers" are isolated nucleic acids that are annealed to a complementary target DNA strand by nucleic acid hybridization to form a hybrid between the primer and the target DNA strand, and then extended along the target DNA strand by a polymerase, e.g., a DNA polymerase. Primer pairs of the present invention refer to their use for amplification of a target nucleic acid sequence, e.g., by the polymerase chain reaction (PCR) or other conventional nucleic-acid amplification methods.

Probes and primers are generally about II nucleotides or more in length, preferably 18 nucleotides or more, more preferably 24 nucleotides or more, and most preferably 30 nucleotides or more. Such probes and primers hybridize specifically to a target sequence under high stringency hybridization conditions. Preferably, probes and primers according to the present invention have complete sequence similarity with the target sequence, although probes differing from the target sequence and that retain the ability to hybridize to target sequences may be designed by conventional methods. Primers and probes are often interchangeable, and so primers may be used as probes and probes may be used as primers where effective. One skilled in the art would know how and when to use a probe as a primer and how and when to use a primer as a probe.

Methods for preparing and using probes and primers are described, for example, in *Molecular Cloning: A Laboratory Manual,* 2nd ed., vol. 1–3, ed. Sambrook et al., Cold Spring Harbor Laboratory Press, Cold Spring Harbor, N.Y., 1989 (hereinafter, "Sambrook et al., 1989"); *Current Protocols in Molecular Biology,* ed. Ausubel et al., Greene Publishing and Wiley-Interscience, New York, 1992 (with periodic updates) (hereinafter, "Ausubel et al., 1992"); and Innis et al., *PCR Protocols: A Guide to Methods and Applications,* Academic Press: San Diego, 1990. Thermal amplification-primer pairs can be derived from a known sequence, for example, by using computer programs intended for that purpose such as Primer (Version 0.5, (c 1991, Whitehead Institute for Biomedical Research, Cambridge, Mass.).

Primers and probes based on the flanking DNA and inserted heterologous sequences disclosed herein can be used to confirm (and, if necessary, to correct) the disclosed sequences by conventional methods, e.g., by re-cloning and sequencing such flanking DNA and inserted sequences.

The nucleic acid probes and primers of the present invention hybridize under stringent conditions to a target DNA sequence. Any conventional nucleic acid hybridization or amplification method can be used to identify the presence of DNA from a transgenic event in a sample. Nucleic acid molecules or fragments thereof are capable of specifically hybridizing to other nucleic acid molecules under certain circumstances. As used herein, two nucleic acid molecules are said to be capable of specifically hybridizing to one another if the two molecules are capable of forming an anti-parallel, double-stranded nucleic acid structure. A nucleic acid molecule is said to be the "complement" of another nucleic acid molecule if they exhibit complete complementarity. As used herein, molecules are said to exhibit "complete complementarity" when every nucleotide of one of the molecules is complementary to a nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Conventional stringency conditions are described by Sambrook et al., is 1989, and by Haymes et al., In: *Nucleic Acid Hybridization, A Practical Approach,* IRL Press, Washington, D.C. (1985). Departures from complete complementarity are therefore permissible, as long as such departures do not completely preclude the capacity of the molecules to form a double-stranded structure. In order for a nucleic acid molecule to serve as a primer or probe it need only be sufficiently complementary in sequence to be able to form a stable double-stranded structure under the particular solvent and salt concentrations employed.

As used herein, a substantially homologous sequence is a nucleic acid sequence that will specifically hybridize to the complement of the nucleic acid sequence to which it is being compared under high stringency conditions. Appropriate stringency conditions which promote DNA hybridization, for example, 6.0× sodium chloride/sodium citrate (SSC) at about 45° C., followed by a wash of 2.0×SSC at 50° C., are known to those skilled in the art or can be found in *Current Protocols in Molecular Biology,* John Wiley & Sons, N.Y. (1989), 6.3.1–6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed. In a preferred embodiment, a nucleic acid of the present invention will specifically hybridize to one or more of the nucleic acid molecules set forth in SEQ ID NOS: 1, 2, 3, 4, 13, 14, and 15 and complements thereof or fragments of either under moderately stringent conditions, for example at about 2.0× SSC and about 65° C. In a particularly preferred embodiment, a nucleic acid of the present invention will specifically hybridize to one or more of the nucleic acid molecules set forth in SEQ ID NOS: 1, 2, 3, 4, 13, 14, or 15 and complements or fragments of either under high stringency conditions. In one aspect of the present invention, a preferred diagnostic or marker nucleic acid molecule of the present invention has the nucleic acid sequence set forth SEQ ID NOS: 1, 2, 3 or 4 and complements thereof or fragments of either. In another aspect of the present invention, a preferred marker nucleic acid molecule of the present invention shares between from about 80% to about 100% or from about 90% to about 100% sequence identity with the nucleic acid sequence set forth in SEQ ID NOS: 1, 2, 3 and 4 and complement thereof or fragments of either. In a further aspect of the present invention, a preferred marker nucleic acid molecule of the present invention shares between from about 95% to about 100% sequence identity with the sequence set forth in SEQ ID NOS: 1, 2, 3 and 4 and complement thereof or fragments of either. SEQ ID NOS: 1, 2, 3 and 4 may be used as markers in plant breeding methods to identify the progeny of genetic crosses similar to the methods described for simple sequence repeat DNA marker analysis, in "DNA markers: Protocols, applications, and overviews: (1997) 173–185, Cregan, et al., eds., Wiley-Liss NY; all of which is herein incorporated by reference in its' entirely. The hybridization of the probe to the target DNA molecule can be detected by any number of methods known to those skilled in the art, these can include, but are not limited to, fluorescent labels (fluorescence emission, fluorescence polarization, and fluorescence quenching), radioactive labels, immunological labels (ELISA and other forms of enzyme linked antibody probes, and incorporated antigen probes such as digoxygenin), and chemiluminescent labels.

Regarding the amplification of a target nucleic acid sequence (e.g., by thermal amplification means) using a particular amplification primer pair, "stringent conditions" are conditions that permit the primer pair to hybridize only to the target nucleic-acid sequence to which a primer having the corresponding wild-type sequence (or its complement) would bind and preferably to produce a unique amplification product, the amplicon, in a DNA thermal amplification reaction.

The term "specific for (a target sequence)" indicates that a probe or primer hybridizes under stringent hybridization conditions only to the target sequence in a sample comprising the target sequence.

As used herein, an "isolated" nucleic acid is one that has been substantially separated or purified away from other nucleic acid sequences in the cell of the organism in which the nucleic acid naturally occurs, i.e., other chromosomal and extrachromosomal DNA and RNA, by conventional nucleic acid-purification methods. The term also embraces recombinant nucleic acids and chemically synthesized nucleic acids.

As used herein, "transformation" refers to the transfer of a nucleic acid fragment into the genome of a host organism such as a host plant, resulting in genetically stable inheritance. Host plants containing the transformed nucleic acid fragments are referred to as "transgenic plants".

As used herein, the term "diagnostic" refers to the fact that, for the purposes of identifying nucleic acid sequences as those contained within or derived from cotton event 757, any one or more of the novel DNA sequences set forth herein comprise the cotton genome flanking sequences adjacent to and linked to the arbitrarily assigned ends of the inserted heterologous DNA sequences are necessary and sufficient as being descriptive as a distinguishing characteristic of the event 757 genome, so long as the sequence comprises at least a part of one of the ends of the inserted heterologous DNA sequence or the cotton genome sequence flanking or adjacent to one of these ends and includes at least the two nucleotides, the di-nucleotide, comprising the point at which the cotton genome sequence and the inserted heterologous DNA sequence are linked together by a phosphodiester bond. It is well known in the art that a sequence that is diagnostic for a particular event, such as those disclosed herein for event 757, which is not present in a particular sample containing nucleic acids, is indicative that the sample does not contain the diagnostic sequence and therefore the nucleic acids in the sample are not or were not derived from and have not been contained within the genome of cotton event 757. In addition, additional novel and diagnostic sequences are present within cotton event 757 DNA as exemplified herein selected from the group consisting of SEQ ID NOS: 1, 2, 3, and 4.

As used herein, "amplified DNA" or "amplicon" refers to the product of nucleic-acid amplification of a target nucleic acid sequence that is part of a nucleic acid template. For example, to determine whether the cotton plant resulting from a sexual cross contains transgenic event genomic DNA from the cotton plant of the present invention, DNA extracted from a cotton plant tissue sample may be subjected to nucleic acid amplification method using a primer pair that includes a first primer derived from sequences in the genome of the plant which are adjacent to one end of the inserted heterologous DNA sequence, and a second primer derived from sequences within the inserted heterologous DNA sequence, to produce an amplicon that is diagnostic for the presence of the event DNA. The amplicon is of a length and has a sequence that is also diagnostic for the event. The amplicon contains at least the di-nucleotide sequence comprising the two nucleotides forming the link between one end of the inserted heterologous DNA and the first nucleotide within the native genome DNA sequence which is immediately adjacent to the end of the inserted heterologous DNA sequence as well as the combined sequences of the first and the second primers. The amplicon may range in length from about five hundred nucleotide base pairs, to about three hundred nucleotide base pairs, to about two hundred nucleotide base pairs, to about fifty nucleotide base pairs, to about the combined length of the primer pairs plus one nucleotide base pair. Alternatively, a primer pair can be derived from flanking sequence within the cotton plant genome sequences linked to both ends of the inserted heterologous DNA sequence so as to produce an amplicon that includes the entire insert nucleotide sequence. A member of a primer pair that is derived from the plant genomic sequence may be located a distance from either end of the inserted DNA sequence, and this distance can range from one nucleotide base pair up to about twenty thousand nucleotide base pairs. In addition, and particular to cotton event 757, are sequences which are diagnostic for the event selected from the group consisting of SEQ ID NO: 1, 2, 3, and 4. The use of the term "amplicon" specifically excludes primer dimers that may be formed in the DNA thermal amplification reaction.

Nucleic-acid amplification can be accomplished by any of the various nucleic-acid amplification methods known in the art, including the polymerase chain reaction (PCR). A variety of amplification methods are known in the art and are described, inter alia, in U.S. Pat. Nos. 4,683,195 and 4,683,202 and in PCR *Protocols. A Guide to Methods and Applications*, ed. Innis et al., Academic Press, San Diego, 1990. Thermal amplification methods have been developed to amplify up to 22 kb of genomic DNA and up to 42 kb of bacteriophage DNA (Cheng et al., Proc. Natl. Acad. Sci. USA 915695-5699, 1994). These methods as well as other methods known in the art of DNA amplification may be used in the practice of the present invention. The sequence of the heterologous DNA insert or flanking sequence from cotton event 757 can be verified (and corrected if necessary) by amplifying such sequences from the event using primers derived from the sequences provided herein followed by standard DNA sequencing of the amplification products.

The amplicon produced by these methods may be detected by a plurality of techniques. One such method is Genetic Bit Analysis (Nikiforov, et al. Nucleic Acid Res. 22:4167–4175, 1994) in which an oligonucleotide is designed which overlaps both the adjacent flanking genomic DNA sequence and the inserted DNA sequence. The oligonucleotide is immobilized in wells of a microwell plate. Following thermal amplification of the region of interest (using a first primer complementary to a part of the inserted sequence and second primer complimentary to a part of the adjacent flanking genomic sequence), a single-stranded amplicon can be used to hybridize to the immobilized oligonucleotide and serve as a template for a single base extension reaction using a DNA polymerase and labelled ddNTPs specific for the expected next base, as determined by fluorescent or immunological based detection methods. A positive signal indicates the presence of the insert/flanking sequence in the sample and is diagnostic for the presence of the event 757 nucleic acid.

Another method for detecting the amplicon diagnostic for the event 757 nucleic acid in a sample is the Pyrosequencing technique as described by Winge (Innov. Pharma. Tech. 00: 18–24, 2000). In this method an oligonucleotide is designed that overlaps the adjacent genomic DNA and insert DNA junction. The oligonucleotide is hybridized to a single-stranded amplicon from the region of interest (amplicon produced using a first primer complimentary to a sequence within the inserted heterologous DNA sequence and a second primer complimentary to a sequence within the flanking genomic sequence) and incubated in the presence of a DNA polymerase, ATP, sulfurylase, luciferase, apyrase, adenosine 5' phosphosulfate and luciferin. dNTPs are added individually and incorporation results in the production of photons of light which are detected and measured, and which is diagnostic for the event 757 nucleic acid sequence in a sample.

Fluorescence Polarization as described by Chen, et al. (Genome Res. 9:492–498, 1999) is a method useful for detecting the diagnostic amplicon of the present invention. Using this method, an oligonucleotide is designed which overlaps the junction of the genomic flanking sequence and inserted DNA sequence. The oligonucleotide is hybridized to a single-stranded thermal amplification product from the region of interest (using a first primer complementary to a part of the inserted heterologous DNA sequence and a second primer complimentary to a part of the genomic DNA sequence flanking the proximal terminal end of the inserted heterologous DNA sequence) and incubated in the presence of a DNA polymerase and a ddNTP labeled with a fluorophore which emits a particular wavelength of light (emission spectrum) upon excitation with light of a wavelength different from the emission spectrum (excitation spectrum). Single base extension results in incorporation of the fluorphore labeled ddNTP. Incorporation can be measured as a change in fluorescence polarization using a fluorimeter. A change in fluorescence polarization indicates the presence of the transgene insert/flanking sequence within the amplicon due to successful amplification, hybridization, and single base extension, and is diagnostic for the event 757 nucleic acid in a sample.

Taqman® (PE Applied Biosystems, Foster City, Calif.) is described as a method of detecting and quantifying the presence of a DNA sequence and sufficiently described in the instructions provided by the manufacturer. Briefly, a FRET (fluorescence resonance emissions tagged) oligonucleotide probe is designed which overlaps the junction at which the reference cotton genomic DNA sequence flanking one end of the inserted heterologous DNA sequence and the end of the inserted heterologous DNA most proximal to the reference cotton genomic DNA sequence are linked. The FRET probe and thermal amplification primers (a first primer complementary to a part of the inserted heterologous DNA sequence and a second primer complementary to a part of the adjacent or flanking cotton genomic DNA sequence) are cycled in the presence of a thermostable polymerase and dNTPs. Hybridization of the FRET probe results in cleavage and release of the fluorescent moiety away from the quenching moiety on the FRET probe. A fluorescent signal indicates the presence of the flanking/transgene insert sequence due to successful amplification and hybridization, and is diagnostic for the presence of the event 757 nucleotide sequence in a sample.

Molecular Beacons have been described for use in sequence detection as described in Tyangi, et al. (Nature Biotech.14: 303–308, 1996). Briefly, a FRET oligonucleotide probe is designed that overlaps the flanking genomic and insert DNA junction. The unique structure of the FRET probe results in a probe exhibiting a secondary structure that maintains the fluorescent and quenching moieties in close proximity. The FRET probe and thermal amplification primers (one primer in the insert DNA sequence and one in the flanking genomic sequence) are cycled in the presence of a thermostable polymerase and dNTPs. Following successful thermal amplification of the amplicon diagnostic for the event 757 DNA sequence, hybridization of the FRET probe to the target sequence results in the removal of the probe secondary structure and spatial separation of the fluorescent and quenching moieties. A fluorescent signal results. A fluorescent signal indicates the presence of the flanking/ transgene insert sequence due to successful amplification and hybridization, and is diagnostic for the event 757 nucleic acid in a sample.

Ligase chain reaction is also contemplated as being diagnostic for the event 757 nucleic acids in a sample.

All of the above methods can be modified to determine the zygosity of a particular sample of nucleic acids derived from a single source. For example, a cotton event 757 plant which is homozygous for the event 757 allele contains within its genome two copies of the event 757 allele characteristic of and diagnostic for the cotton event 757 genome, and thus when selfed would breed true. Alternatively, a cotton event 757 homozygous plant can be crossed with another variety of cotton, and the result of that cross would be plants that were heterozygous for the event 757 allele. Methods are envisioned in which one skilled in the art could determine the zygosity of a particular plant with reference to the event 757 allele. This method requires at least three oligonucleotide sequences as set forth herein. For example, a heterozygosity assay comprising a thermal amplification reaction comprising event 757 nucleic acid sequences in a sample as the template and Primer G (SEQ ID NO: 9) and Primer H (SEQ ID NO: 10) described herein would produce an amplicon of about 682 base pairs in length, which is diagnostic for the presence of event 757 DNA in a sample. The addition in the same thermal amplification reaction of an additional primer sequence comprising, for example, Primer G and Primer J (SEQ ID NO: 12) should produce an amplicon which is about 1195 base pairs in length if a cotton genome comprising DNA sequence other than event 757 DNA is also present in the sample, which is diagnostic for the presence of native cotton DNA sequence in a sample. Herein, the inventors have determined as judged by molecular characterization that cotton event 757 contains a primary functional insert containing a significant portion of the transformation plasmid, PV-GHBK04 (FIG. 1). A secondary, nonfunctional insertion, includes a right border initiation event that continues up to and is linked with the 7S 3' transcriptional termination sequence and 3' of the Cry1A coding sequence within the primary functional insertion.

The inventors herein describe the molecular analyses that have been performed on transgenic cotton event 757 to further define the ends of the T-DNA insertions and identify the cotton genomic DNA flanking the T-DNA insertions. Genome walking studies combined with nucleotide sequencing has resulted in the identification of the DNA sequences at the arbitrarily assigned 5' and 3' ends of the primary, functional insert, as well as cotton genomic DNA flanking the 5' (767 nucleotides) and 3' (307 nucleotides) ends of the T-DNA insertions in the transgenic cotton event 757. The second, nonfunctional, T-DNA insertion, containing a portion of the Cry1A coding region, is located at the arbitrarily assigned 5'end (7S 3' portion) of the primary insert. A 256 base pair fragment of the e35S promoter associated with the first 1111 base pairs of a Cry1 A coding region is also present and linked to both the primary functional insert and to the secondary non-functional inserted sequence. This additional sequence is located between, and is contiguous with, the T-DNA insertions. These results suggest the presence of multiple segments of T-DNA from plasmid PV-GHBK04 at a single point of insertion in the genome of the transgenic cotton event 757. The linkage between the various elements at the point of insertion was confirmed using Southern blot and thermal amplification analysis.

The inventors therefore disclose herein the analysis of the genome architecture of the inserted sequence and flanking cotton genomic DNA sequences in transgenic cotton event 757 including over 767 base pairs of cotton genomic DNA flanking the arbitrarily assigned 5'end of the insertion and over 307 base pairs of cotton genomic DNA flanking the arbitrarily assigned 3'end of the insertion event in cotton event 757. In addition, a second inserted sequence containing a part of the 3' coding region for a Cry1A nucleic acid sequence is present in proximity to the arbitrarily assigned 5'-end (7S 3' portion) of the primary insert, and additionally a 256 base pair fragment of the e35S promoter associated with the first 1111 base pairs of the Cry1Ac coding region present in PV-GHBK04 are positioned between the primary and secondary inserted DNA sequences, thus defining a complex arrangement of genetic elements derived from the transformation plasmid PV-GHBK04 at a single point of insertion in the genome of the transgenic cotton event 757.

A method for producing a cotton plant that is resistant to *Lepidoptera* insect infestation may be conducted with the following steps: I) sexually crossing a first cotton plant grown from the cotton seed PV-GHBK04 (EVENT 757) comprising a DNA molecule selected from the group consisting of SEQ ID NO: 13, SEQ ID NO: 14, and SEQ ID NO: 15 that confers resistance to *Lepidoptera* insect infestation, and a second cotton plant that lacks the resistance to *Lepidoptera* insect infestation, thereby producing a plurality of first progeny plants; 2) selecting a first progeny plant that is resistant to *Lepidoptera* insect infestation; 3) selfing said first progeny plant, thereby producing a plurality of second progeny plants; and 4) selecting from said second progeny plants a plant resistant to *Lepidoptera* insect infestation. The first progeny plant that is resistant to *Lepidoptera* insect infestation or the second progeny plant that is resistant to *Lepidoptera* insect infestation may be backcrossed to the second cotton plant or a third cotton plant and a cotton plant that is resistant to *Lepidoptera* insect damage infestation be produced.

DNA detection kits can be developed using the compositions disclosed herein and the methods well known in the art of DNA detection. The kits are useful for identification of cotton event 757 DNA in a sample and can be applied to methods for breeding cotton plants containing 757 DNA. The kits contain one or more DNA sequences comprising at least 11 contiguous nucleotides homologous or complementary to sequences selected from the group consisting of SEQ ID NO: 13, SEQ ID NO: 14, and SEQ ID NO: 15 or complements thereof, these DNA sequences can be used in DNA amplification reactions or as probes in a DNA hybridization method.

In addition to the above discussed procedures, practitioners are familiar with the standard resource materials which describe specific conditions and procedures for the construction, manipulation and isolation of macromolecules (e.g., DNA molecules, plasmids, etc.), generation of recombinant organisms and the screening and isolating of clones (see, for example, Sambrook et al., Molecular Cloning: A Laboratory Manual, Cold Spring Harbor Press, 1989; Mailga et al., Methods in Plant Molecular Biology, Cold Spring Harbor Press, 1995: Birren et al., Genome Analysis: Analyzing DNA, 1, Cold Spring Harbor, N.Y., 1997).

The following examples are included to demonstrate certain preferred embodiments of the invention. It should be appreciated by those of skill in the art that the techniques disclosed in the examples that follow represent approaches the inventors have found function well in the practice of the invention, and thus can be considered to constitute examples of preferred modes for its practice. However, those of skill in the art should, in light of the present disclosure, appreciate that many changes can be made in the specific embodiments that are disclosed and still obtain a like or similar result without departing from the spirit and scope of the invention.

EXAMPLES

Example 1.

Cotton event PV-GHBK04 (757)

*Lepidoptera* species infestation of cotton fields exerts a negative impact on cotton production. Cotton species, and in particular *Gossypium hirsutum*, have been genetically modified to resist *Lepidoptera* insect infestation. One means for producing plants, which are resistant to insect infestation comprises the insertion of a DNA cassette that contains a sequence encoding an insecticidal Cry1A protein, derived from the bacterium *Bacillus thuringiensis* into the genome of cotton cultivar Coker 312. Cotton plants can be transformed using a variety of means, however, in this case cotton plants were transformed using an *Agrobacterium tumefaciens* mediated transformation system using a DNA fragment derived from plasmid PV-GHBK04 (pMON 10518 in U.S. Pat. No. 5,500,365). Plant selection after transformation of cotton cells and regeneration of transgenic plants resulted in the instant insect resistant cotton event 757.

Molecular analyses were performed on cotton event 757 to define the ends of the transgene DNA insertions and identify the cotton genomic DNA flanking the transgene DNA inserts. Genome walking studies combined with nucleotide sequencing yielded the DNA sequences of the 5' and 3' ends of the primary, functional insert, as well as cotton genomic DNA flanking the 5' (767 base pair) and 3' (307 base pair) ends of the transgene DNA insertions in cotton event 757. The results from these genome walking experiments suggested the presence of multiple segments of transgene DNA from plasmid PV-GHBK04 at a single point of insertion in the genome of cotton event 757. The linkage between the various elements at the point of insertion was confirmed using Southern blot and thermal amplification analysis. The resulting complex arrangement of genetic elements, derived from the transformation plasmid PV-GHBK04 at a single point of insertion, in cotton event 757 provides novel nucleic acid sequences both within the inserted DNA itself and at the junction of inserted DNA and cotton genomic DNA. These novel nucleic acid sequences are useful for detecting DNA from cotton event 757 in a sample using various methods well known in the art. The test substance for this study was the insect resistant cotton event 757. The control substance was the non-transgenic cotton line Coker 312 which was used as the recipient of the PV-GFIBKO4 genetic material. The reference substances included the plasmid PV-GHBK04 that was used in the transformation of cotton event 757. Southern blot analyses were performed with genomic cotton DNA, in which 17 picograms and 34 picograms of plasmid PV-GHBK04 (~0.5 and 1 genome copy equivalents, respectively) was mixed with DNA from the Coker control event, digested, and separated by electrophoresis on agarose gels. Additionally, molecular weight markers (Boehringer Mannheim) [molecular size markers E (23.1 Kb0.6 Kb) and IX (1.4 Kb–0.072 Kb), catalog #236 250 and #1449 460, respectively] and Gibco BRL [High Molecular Weight DNA Markers (48.5 Kb–8.3 Kb), catalog # 15618-010] were used for size estimations on Southern blots, while Gibco BRL 1 Kb DNA Ladder (12.2 Kb–0.5 Kb), catalog # 15615-016, and 100 bp DNA Ladder (2.1 Kb–0.1 Kb), catalog #15628-050 were used for size estimations in PCR and RT-PCR analyses.

Example 2

Restriction Enzyme Digestion of Genomic DNA

Approximately 10 µg of genomic DNA from each of the test and control lines was used for restriction enzyme digestions. Overnight digests were performed according to the manufacturers' instructions in a total volume of 500 µL using 100 units of the appropriate restriction enzyme. After digestion, the samples were precipitated by adding 1/10 volume (~50 μL) of 3 M NaOAc, pH 5.2, and 2 volumes (~1 mL relative to the original digest volume) of 100% ethanol, followed by incubation in a −20° C. freezer for at least one hour. The digested DNA was pelleted at maximum speed in a microcentrifuge, washed with 70% ethanol, vacuum dried for approximately 4 minutes, and re-dissolved at room temperature in water.

Example 3

DNA Probe Preparation for Cotton Event 757 Genomic DNA Southern Blots

Four DNA probe templates were prepared by thermal amplification using PV-GHBK04 as a template. The probes were designed to collectively span nearly the entire sequence of PV-GHBK04 (FIG. 1). Approximately 25 ng of each probe template were labeled with $^{32}$P-dCTP (6000 Ci/mmol) using a random priming method (RadPrime DNA Labeling System, Gibco BRL, Gaithersburg Md.). All radiolabeled probes were purified using a Sephadex G-50 column (Boehringer Mannheim).

Example 4

DNA Isolation from Cotton Event 757 for Southern Blot and Thermal Amplificatoin Analyses DNA from the test substance was extracted from seed tissue. DNA was extracted from both seed and leaf tissues from the control substance. DNA from seed was isolated by processing the seed to a fine powder using a commercially available blender. Approximately 2 g of the processed seed was transferred to a 50 mL conical tube, and ~16 mL of CTAB extraction buffer [1.5% (w:w) CTAB, 75 mM Tris-HCl pH 8.0, 100 mM EDTA pH 8.0, 1.05 M NaCl, and 0.75% (w:w) PVP (MW 40,000)] was added to the processed seed. The samples were incubated at 65° C. for approximately 30 minutes with intermittent mixing and then allowed to cool to room temperature. An equal volume (~16 mL) of room temperature chloroform:isoamyl alcohol (24:1 (v/v)) or chloroform was added to the samples. The suspension was mixed by inversion, and the two phases separated by centrifugation at ~16,000×g for 5 minutes. The aqueous (top) layer was removed using a transfer pipette and placed into a clean 50 mL conical tube. Approximately ⅟₁₀ volume (~1.6 mL) of 10% CTAB buffer [10% (w:w) CTAB and 0.7 M NaCl] was added to the aqueous phase, which was then mixed by inversion. The samples were centrifuged at ~16,000×g for 5 minutes to separate the phases. The aqueous (upper) phase was removed, mixed with an equal volume (~15 mL) of CTAB precipitation buffer [1% (w:w) CTAB, 50 mM Tris pH 8.0, and 10 mM EDTA pH 8.0] and allowed to stand at room temperature for approximately 1 hour. The samples were centrifuged at ~10,000×g to pellet the DNA, the supernatant was decanted, and the pellet was dissolved in approximately 2 mL of high salt TE [10 mM Tris-HCl pH 8.0, 10 mM EDTA pH 8.0, and 1 M NaCl] by incubating at 37° C. with gentle swirling for approximately 2 hours. Centrifugation was performed at ~23,000×g to pellet any remaining impurities. The supernatant was removed, placed into a clean 15 mL tube, and approximately ⅟₁₀ volume (~150 μL) of 3M NaOAc, pH 5.2, and 2 volumes (~4 mL relative to the supernatant) of chilled 100% ethanol were added to precipitate the DNA. The precipitated DNA was spooled into a microfuge tube containing approximately 1 mL of 70% ethanol. The DNA was pelleted in a microfuge at maximum speed (14,000 rpm) for 5 minutes, dried, and re-dissolved in TE, pH 8.0 in a 4° C. refrigerator overnight.

The Coker 312 genomic DNA used as a control for Southern blot analysis was isolated from leaf tissue that was frozen in liquid nitrogen and ground into a fine powder using a mortar and pestle. Approximately 1 g of the ground leaf tissue was transferred to a 13 mL centrifuge tube and 6 mL of extraction buffer [2.5 mL DNA extraction buffer (350 mM sorbitol, 100 mM Tris pH 7.5, 5 mM EDTA, 0.38% (w/v) sodium bisulfite), 2.5 mL nuclei lysis buffer (200 mM Tris pH 7.5, 50 mM EDTA, 2 M NaCl, 2% (w/v) CTAB), and 1 mL Sarkosyl (5% (w/v) solution)] was added. The samples were incubated at 65° C. for approximately 30 minutes with intermittent mixing. Four and a half milliliters of chloroform:isoamyl alcohol (24:1 (v/v)) at room temperature was added to the samples. The suspension was mixed for 2 to 3 minutes, and the two phases separated by centrifugation for 15 minutes at ~2,000×g at 4° C. The aqueous (top) layer was removed using a transfer pipette and placed into a 13 mL centrifuge tube. Five milliliters of 100% isopropanol were added, and the tubes were mixed by inversion to precipitate the DNA. The precipitated DNA was spooled into a microfuge tube containing 500 ?L of 70% ethanol. The DNA was pelleted in a microfuge at maximum speed (14,000 rpm) for 2 minutes. The DNA was dried and dissolved in TE buffer in a 4° C. refrigerator overnight.

Example 5

Southern Blot Analysis of Genomic Cotton DNA

Southern blot analyses (Southern, J. Mol. Biol. 98: 503–17, 1975) were performed according to standard procedures. The samples of DNA digested with restriction enzymes were separated, based on size, using 0.8% agarose gel electrophoresis. A "long run" and a "short run" were performed for each Southern blot analysis. The long run facilitated greater resolution of the higher molecular weight DNA fragments while the short run ensured that all smaller molecular weight DNA fragments were retained on the gel. The gels were subjected to 85 V for ~5 hours then to 38 V for ~12 hours, then stained in a buffer containing ethidium bromide.

After photographing, the gel was placed in a depurination solution (0.125 N HCl) for approximately 10 minutes followed by a denaturing solution (0.5 M NaOH, 1.5 M NaCl) for 30 minutes and then a neutralizing solution (0.5 M Tris-HCl pH 7.0, 1.5 M NaCl) for 30 minutes. The DNA from the agarose gels was transferred to Hybond-N nylon membranes (Amersham, Arlington Heights, Ill.) using a Turboblotter™ (trademark of Schleicher & Schuell, Keene, N. H.). The DNA was allowed to transfer for 4–6 hours (using 20×SSC as the transfer buffer) and covalently cross-linked to the membrane with a UV Stratalinker 1800 (Stratagene, La Jolla, Calif.), using the auto crosslink setting. The blots were prehybridized for 0.5–2 hours at ~65° C. in an aqueous solution of 500 mM $Na_2HPO_4.7H_2O$, 7% SDS, and 0.1 mg/mL tRNA. Hybridization with the radiolabeled probe was performed in fresh prehybridization solution for 16–17 hours at approximately 65° C. Membranes were washed in an aqueous solution of 0.1% SDS and 0.1×SSC for two ~15 minute periods followed by two ~20 minute periods at approximately 65° C. using fresh solution for each of the four washes. Multiple exposures of the blots were then generated using Kodak Biomax MS film in conjunction with one Kodak Biomax MS intensifying screen at approximately −80° C.

Four Southern blots were generated to demonstrate the linkage and structure of the refined cotton event 757 insert map.

1. Southern Blot Analysis—Probe 1.

Genomic DNA from the test substance was digested with ScaI, SspI, and SphI restriction endonucleases. DNA from Coker 312 and Coker 312 mixed with plasmid PV-GHBK04 was digested with SspI. These digestions were loaded into agarose gels and prepared for Southern analysis as described above, using a $^{32}$P-labeleled Probe 1 (FIG. 1). As expected, no detectable hybridization was observed in the Coker 312 non-transgenic control long-run. Plasmid PV-GHBK04 mixed with Coker 312 in the short run produced the expected ~7.8 Kb band (FIG. 1). Both the cotton event 757/ScaI long and short runs produced a faint 2.6 Kb band and a >23 Kb border band. The cotton event 757/SspI long and short runs produced two predicted bands at 7.4 and 4.2 Kb (faint) and an expected border band at 4.7 Kb. The cotton event 757/SphI long and short runs produced three predicted bands at 6.3, 4.9, and 4.2 Kb (faint). A slight alteration in the migration pattern of the molecular weight markers was observed in the long run samples. However, the nucleotide sequence had been obtained for the unique junctions and the intervening DNA sequences before Southern analysis, the anomalous marker migration did not affect the interpretation of the results.

2. Southern Blot Analysis—Probe 2.

The blots described above were stripped and re-probed with P-labeled Probe 2 (see FIG. 1). As expected, no detectable hybridization was observed in the Coker 312 non-transgenic control long-run. Plasmid PV-GHBK04 mixed with Coker 312 in the short run produced the expected band at ~7.4 Kb (FIG. 1). Both the cotton event 757/ScaI long and short runs produced three predicted bands at 3.4, 2.6 (faint), and 1.5 Kb and an expected border band at >23 Kb. The lower level of hybridization to the >23 Kb band is presumed to result from the lower efficiency of transfer of high molecular weight DNA. The cotton event 757/SspI long and short runs produced two predicted bands at 7.4 and 4.2 Kb. The cotton event 757/SphI long and short runs produced three predicted bands at 6.3, 4.9 (faint), and 4.2 Kb. A fourth band was observed at −10.5 Kb. This band was consistent with incomplete digestion at the SphI restriction site at the end of the 7S 3' transcriptional termination element of the full-length Cry1A coding region. Incomplete cleavage at this site would result in an ~10.5 Kb band that would only show hybridization with Probes 2 and 3 (see FIG. 3). This conclusion is corroborated by the results using Probe 3.

3. Southern Blot Analysis—Probe 3.

The blots were stripped and re-probed with a $^{32}$P-labeled Probe 3 (see FIG. 1). As expected, no detectable hybridization was seen in the Coker 312 non-transgenic control long-run. Plasmid PV-GHBK04 mixed with Coker 312 in the short run produced the expected bands at −7.4 and −4.0 Kb (FIG. 1). The cotton event 757/ScaI long run produced three predicted bands at 3.4, 2.6, 1.5 (faint) Kb and an expected faint border band at 9.4 Kb. The cotton event 757/ScaI short run produced the same three predicted bands and border band, and an additional band at 0.2 Kb which is no longer present on the gel in the long run lane. The cotton event 757/SspI long and short runs produced two predicted bands at 7.4 and 4.2 Kb. The cotton event 757/SphI long and short runs (Lanes 4 and 9) produced two predicted bands at 6.3 and 4.2 Kb. A third band can be seen at −10.5 Kb which is a result of incomplete digestion (see discussion of Probe 2).

4. Southern Blot Analysis—Probe 4.

The blots were stripped and re-probed with a $^{32}$P-labeled Probe 4 (see FIG. 1). As expected, no detectable hybridization was seen in the Coker 312 non-transgenic control long-run. Plasmid PV-GHBK04 mixed with Coker 312 in the short run produced the expected band at −4.0 Kb (FIG. 1). The cotton event 757/ScaI long and short runs produced an expected border band at >23 Kb. The cotton event 757/SspI long and short runs produced an expected border band at 4.6 Kb. The cotton event 757/SphI long and short runs produced the predicted band at 4.9 Kb.

Example 6

Identification and Verification of Insertion Sequence Junctions with Cotton Genome Sequence in Cotton Event 757

Figure 3:
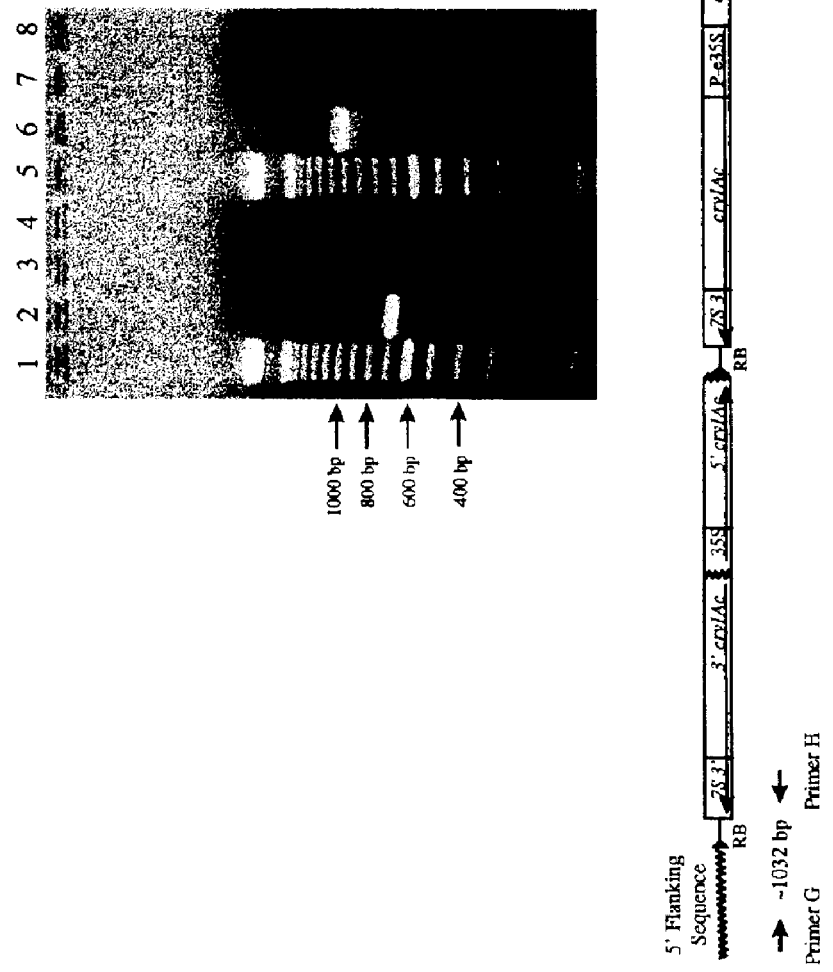
FIG. 3 illustrates the linear map as set forth in FIG. 2 and indicates two primer pairs (Primer G and Primer H, and Primer I and Primer J) each set out in positions below the linear map in approximate locations where each primer hybridizes to the sequence of the inserted DNA, each oriented in the direction of primer extension. The size in base pairs of the event specific diagnostic amplicon produced upon thermal amplification of the indicated region using the indicated primer pairs is indicated between each primer pair. The photograph above the linear map illustrates the electrophoretic profile of nucleic acid amplicons produced using these primer pairs and DNA extracted from cotton event 757 as template. Lane 1 and 5: GIBCO BRL 100 base pair ladder; Lane 2: 682 base pair amplicon product using DNA extracted from cotton event 757 and primer pair I and J; Lanes 3 and 4: primer pair I and J and (3) Coker 312 non-transgenic DNA template or (4) no template; Lane 6: 1032 base pair amplicon product using DNA extracted from cotton event 757 and primer pair G and H; Lanes 7 and 8: primer pair G and H and (7) Coker 312 non-transgenic DNA template or (8) no template.

The DNA sequences at the arbitrarily assigned 5' end of the primary insert and the genomic DNA flanking the arbitrarily assigned 5' end of the insert (5'GTTTGCTTGGACACTGATAG 3', SEQ ID NO: 1) and the arbitrarily assigned 3' end of the primary insert and the genomic DNA flanking the arbitrarily assigned 3' end of the insert (5'AAACCCTTTCTGGAAAAATA3', SEQ ID NO-2) were identified using the Universal GenomeWalker Kit™ according to the manufacturer's protocol, followed by nucleotide sequencing of the amplicon products. Thermal amplification assays were developed using a first primer complementary to cotton genomic DNA and a second primer complementary to inserted transgene DNA. For example, a first primer corresponding to a part of the arbitrarily assigned 5' genomic flanking sequence (5'GAGAGAGATAGGCACTAAAGTAAGCA3', SEQ ID NO: 9) was paired with a second primer at the arbitrarily assigned 5' end of the primary insert (5'TTAGACAAATTGTCACGGTCTACCAGAA3', SEQ ID NO: 10); a third primer corresponding to a part of the arbitrarily assigned 3' genomic flanking sequence (5'TTGATGCACTTACGAAAGAAGAACCGA3', SEQ ID NO: 12) was paired with a fourth primer corresponding to a part of the sequence of the arbitrarily assigned 3' end of the primary insert (5'TTCCCAACGATCAAGGCGAGTTAC3', SEQ ID NO: 11) (FIG. 3).

The thermal amplification assays were performed using 100 ng of cotton event 757 genomic DNA template in a 50 µL reaction volume containing a final concentration of 1.5 mM Mg$^{2+}$, 0.2 µM of each primer, 200 µM each dNTP, and 1 unit of Taq DNA polymerase. The reactions amplifying an amplicon diagnostic for the arbitrarily assigned 5' flanking sequence were performed under the following cycling conditions: 1 cycle at 94° C. for 2 minutes; 35 cycles of 94° C. for 1 minute, 48° C. for 1 minute, 72° C. for 3 minutes; 1 cycle at 72° C. for 10 minutes. The reactions amplifying an amplicon diagnostic for the arbitrarily assigned 3' flanking sequence were performed under the following cycling conditions: 1 cycle at 94° C. for 2 minutes; 30 cycles of 94° C. for 1 minute, 55° C. for 1 minute, 72° C. for 2 minutes; 1 cycle at 72° C. for 10 minutes. The amplicon produced from each of these reactions were resolved using agarose gel electrophoresis, visualized by ethidium bromide staining, excised from the gel, and subjected to DNA sequencing using dye-terminator chemistry to confirm the sequences.

TABLE 1

Thermal amplification procedure and reaction mixture for obtaining an amplicon from cotton event 757 arbitrarily assigned 5' end sequence inserted into the cotton genome and containing the transgene insert/genome junction sequence diagnostic for the event:

| Step | Reagent | Amount | Comments |
| --- | --- | --- | --- |
| 1 | Nuclease-free water | add to final volume of 50 µL | — |
| 2 | 10X reaction buffer (with MgCl$_2$) | 5.0 µL | 1X final concentration of buffer, 1.5 mM final concentration of MgCl$_2$ |
| 3 | 10 mM solution of dATP, dCTP, dGTP, and dTTP | 1 µL | 200 µM final concentration of each dNTP |
| 4 | each primer (resuspended in 1X TE buffer or nuclease-free water to a concentration of 10 µM) | 1 µL each | 0.2 µM final concentration |
| 5 | Taq DNA polymerase (1 unit/µL) | 0.5 µL (recommended to switch pipettes prior to next step) | 1 unit/reaction |

TABLE 1-continued

Thermal amplification procedure and reaction mixture for obtaining an amplicon from cotton event 757 arbitrarily assigned 5' end sequence inserted into the cotton genome and containing the transgene insert/ genome junction sequence diagnostic for the event:

| Step | Reagent | Amount | Comments |
|---|---|---|---|
| 6 | Extracted DNA (template): Samples to be analyzed | — | |
| | Seed tissue | 50–200 ng of genomic DNA | |
| | Leaves (Negative control) | 100 ng of cotton genomic DNA (not 757) | |
| | Seed (Negative control) | no DNA template solution | |
| | Seed (Positive control) | 50–200 ng of 757 genomic DNA | |

Gently mix and, if needed (no hot top on thermocycler), add 1–2 drops of mineral oil on top of each reaction. Proceed with the amplification reaction in a Stratagene Robocycler, MJ Engine, Perkin-Elmer 9700, or Eppendorf Mastercycler Gradient thermocycler using the following cycling parameters (Table 2).

TABLE 2

Amplification parameters

| Cycle No. | Settings: Stratagene Robocycler | |
|---|---|---|
| 1 | 94° C. | 2 minutes |
| 35 | 94° C. | 1 minute |
| | 48° C. | 1 minute |
| | 72° C. | 3 minute |
| 1 | 72° C. | 10 minutes |

As expected, the control reactions without template DNA and Coker 312 non-transgenic negative control DNA did not generate an amplification product. The cotton event 757 samples generated the expected size amplicons of 1032 base pairs for the arbitrarily assigned 5' end flanking sequence and 682 base pairs for the arbitrarily assigned 3' end flanking sequence. Therefore, the novel nucleic acid sequences at the junction of inserted DNA and cotton genomic DNA in cotton event 757 are useful for detecting DNA derived from cotton event 757 in a sample and are diagnostic for the presence of cotton event 757 DNA in a sample. Those of skill in the art, in light of this example, should appreciate that many changes can be made to the foregoing thermal amplification assays to detect DNA derived from cotton event 757 in a sample. For example, a thermal amplification primer set comprising one primer complementary to cotton genome DNA flanking the heterologous insert DNA sequence and another primer complementary to novel nucleic acid sequences within the DNA inserted into the genome during the transformation process, said primers consisting of SEQ ID NO: 3 (5'TGTTCTGTGGAAAAGGAAGG3') and SEQ ID NO: 4 (5'ATGCCTGCAGGTCAATTCAA3'), are envisioned. Furthermore, any of various hybridization assays described earlier using DNA probes complementary to said novel nucleic acid sequences are envisioned as well.

Figure 4:
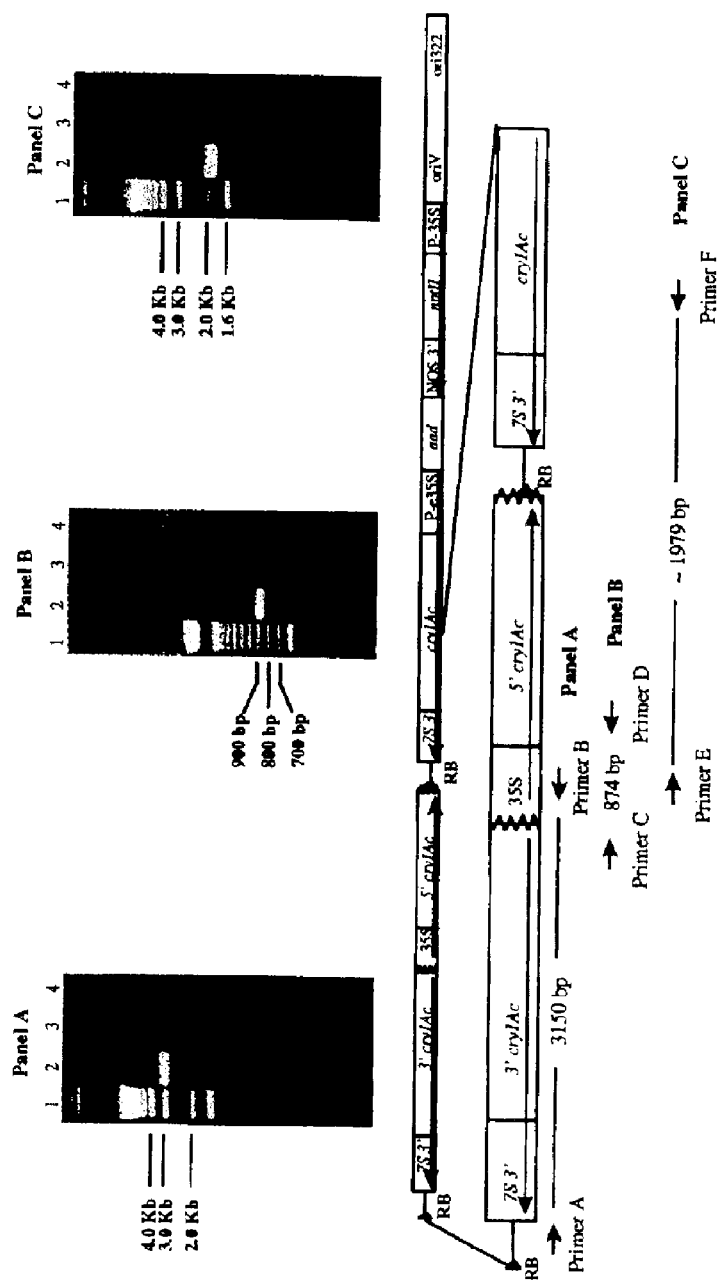
FIG. 4 illustrates thermal amplification analyses of the inserted heterologous DNA present in cotton event 757 using three different primer sets (A and B, C and D, and E and F) to verify the presence of junction sequences diagnostic for event 757. The linear map of the inserted heterologous DNA present in event 757 as set forth in FIG. 2 is shown along with an expanded linear map of the arbitrarily assigned 5' end one half of the linear map depicted below the FIG. 2 linear map. Primer A and Primer B, when used as a primer pair in a thermal amplification reaction with event 757 DNA as template, produce a diagnostic amplicon of 3150 base pairs, as illustrated in Lane 2 in Panel A. Primer C and Primer D, when used as a primer pair in a thermal amplification reaction with event 757 DNA as template, produce a diagnostic amplicon of 874 base pairs, as illustrated in Lane 2 in Panel B. Primer E and Primer F, when used as a primer pair in a thermal amplification reaction with event 757 DNA as template, produce a diagnostic amplicon of 1979 base pairs, as illustrated in Lane 2 in Panel C. Each Panel represents the results of control and test samples after amplification reaction with various templates and indicated primer pairs. In each Panel, lane 3 represents the indicated primer pair along with Coker 312 non-transgenic DNA as template, and lane 4 represents the indicated primer pair with no template.

As expected from the data presented in FIG. 4, the control reactions without template and Coker 312 non-transgenic negative control DNA did not generate a thermal amplification reaction product in either of the analyses. The cotton event 757 samples generated the expected size thermal amplification products of 1032 base pairs for the arbitrarily assigned 5' end flanking sequence and 682 base pairs for the arbitrarily assigned 3' end flanking sequence (see diagram at bottom of FIG. 3). The thermal amplification products from similar reactions were subjected to DNA sequencing. The resulting sequences are exemplified in SEQ ID NO: 13 and SEQ ID N014 containing the arbitrarily assigned 5' end and arbitrarily assigned 3' ends which are inserted into cotton genomic DNA sequences, respectively. In addition to the 139 nucleotides of 7S and right border region which were identified by DNA sequence analysis and set forth in SEQ ID NO: 5, 767 nucleotides of the cotton genomic DNA adjacent to the arbitrarily assigned 5' end of the inserted DNA is exemplified in SEQ ID NO:6. SEQ ID NO:7 sets forth the sequence of 206 nucleotides of the PV-GHBK04 backbone sequence which are at the arbitrarily assigned 3' end of the inserted DNA in cotton event 757 and which are adjacent to 307 nucleotides of cotton genomic DNA (SEQ ID NO: 8).

Example 10

Verification of other Unique Junctions in Cotton Event 757

Overlapping thermal amplification products were generated and sequenced to verify the linkage between elements at the arbitrarily assigned 5' end of the cotton event 757 insert. All amplification products were separated using agarose gel electrophoresis and subjected to DNA sequencing using dye-terminator chemistry (Monsanto Genomics Sequencing Center) to confirm the sequences.

1. Demonstration of the Linkage Between the DNA Flanking the Arbitrarily Assigned 5' End of the Insert and a Partial P-e35S Element Thermal amplification was used to demonstrate the linkage between the DNA flanking the arbitrarily assigned 5' end of the insert and partial e35S promoter. Thermal amplification was conducted using a primer pair Primer A (5'GACTTCCCATCTCTATCC3', SEQ ID NO: 16) and Primer B (5'ATTGTGCGTCATCCCTTAC3', SEQ ID NO: 17) (FIG. 4) on 33 ng of cotton event 757 genomic DNA template in a 50 µL reaction volume containing a final concentration of 1.5 mM $Mg^{2+}$, 0.4 µM of each primer, 200 µM each dNTP, 1 µL of DMSO, and 5 units of Taq DNA polymerase. The reactions for verification were performed under the following cycling conditions: 1 cycle at 94° C. for 3 minutes; 35 cycles of 94° C. for 1 minute, 54° C. for 1 minute, 72° C. for 3.5 minutes; 1 cycle at 72° C. for 10 minutes.

2. Demonstration of the Linkage Between the Partial 3' Cry1Ac Element and the Partial 5' Cry1Ac Element Thermal amplification was used to demonstrate the linkage between the partial 3' cry1Ac sequence and the partial 5' cry1Ac sequence. Thermal amplification was conducted using a primer pair Primer C (5'GAATAGGGGTCACAGAAGCATA3', SEQ ID NO: 18) and Primer D (5'GGACCAAAGATACCCCAGAT3', SEQ ID NO: 19) (FIG. 4) on 33 ng of cotton event 757 genomic DNA template in a 50 µL reaction volume containing a final concentration of 1.5 mM $Mg^{2+}$, 0.2 µM of each primer, 200 µM each dNTP, 1 µL of DMSO, and 5 units of Taq DNA polymerase. The reactions for verification were performed under the following cycling conditions: 1 cycle at 94° C. for 3 minutes; 35 cycles of 94° C. for 1 minute, 55° C. for 1 minute, 72° C. for 1 minute; 1 cycle at 72° C. for 10 minutes.

3. Demonstration of the Linkage Between the Partial P-e35S Element and the Full-Length Cry1Ac sequence.

Thermal amplification was used to demonstrate the linkage between the partial e35S promoter and the full-length Cry1Ac coding region. Thermal amplification was conducted using primer pair Primer E (5ATAAAGGAAAGGCCATCGT3', SEQ ID NO: 20) and Primer F (5'AGTACTTrCCTGAGACCGACAAAGT3', SEQ ID NO: 21) (FIG. 4) on 33 ng of cotton event 757 genomic DNA template in a 50 µL reaction volume containing a final concentration of 1.5 mM $Mg^{2+}$, 0.2 µM of each primer, 200 µM each dNTP, 1 µL of DMSO, and 5 units of Taq DNA polymerase. The reactions for verification were performed under the following cycling conditions: 1 cycle at 94° C. for 3 minutes; 35 cycles of 94° C. for 1 minute, 54° C. for 1 minute, 72° C. for 2 minutes; 1 cycle at 72° C. for 10 minutes.

The thermal amplification-based technique genome walker was used to generate amplification products containing cotton genomic DNA at the 5' and 3' ends of the inserted DNA. While performing this analysis, an additional segment of cry1Ac sequence associated with a partial e35S promoter was identified. Three overlapping thermal amplification products were generated and subjected to DNA sequencing to validate the linkage among the elements in the 5' region of the cotton event 757 insert. The resulting consensus sequence is exemplified by SEQ ID NO: 15. These results add further definition to the previously reported insertion map of cotton event 757. Specifically, the partial 3' Cry1Ac coding region associated with an intact 7S 3' transcriptional termination sequence is shown to be located in proximity to the right border region of the primary T-DNA insert. Additionally, this 3'Cry1Ac coding region is separated from the functional portion of the insert by a portion of the e35S promoter contiguous with a portion of the 5'Cry1Ac coding region.

Three different thermal amplification analyses were performed using genomic DNA from cotton event 757, line Coker 312, or no template. The results of these analyses are shown in the Panels in FIG. 4. First, linkage between the 5' cotton genomic DNA flanking sequence, through the 7S transcriptional termination sequence and partial 3' cry1Ac sequence, to the partial e35S promoter was verified using Primers A and B, and shown in Panel A of FIG. 4. Next, the 3' partial cry1Ac sequence, through the partial e35S promoter, to the 5' partial cry1Ac sequence linkage was demonstrated using Primers C and D, and shown in Panel B of FIG. 4. Finally, the partial e35S promoter and 5' partial cry1Ac sequence were linked to the full-length cry1Ac sequence of the primary insert using Primers E and F, and shown in Panel C of FIG. 4. The positions of all primers as well as the results of all thermal amplification analyses are shown in FIG. 4. As expected, the Coker 312 non-transgenic negative control DNA and the control reactions without template and (Lanes 3 and 4 in all panels, respectively) did not generate an amplification product in any of the analyses. The cotton event 757 sample generated the expected size amplicon products of 3150 base pairs for the arbitrarily assigned 5' cotton genomic DNA flanking sequence to partial e35S promoter product (FIG. 4, Panel A, Lane 2), 874 base pairs for the partial 3' Cry1Ac coding region to the partial 5' Cry1Ac coding region product (FIG. 4, Panel B, Lane 2), and 1978 base pairs for the partial e35S promoter to full-length Cry1Ac coding region product (FIG. 4, Panel C, Lane 2). The amplicons from similar reactions were subjected to DNA sequencing. The combined DNA sequences establish the unique junctions as set forth in SEQ ID NO: 15. The nucleotide positions for the linkage and orientation of genetic elements in SEQ ID NO: 15 are as follows: nucleotide position 1 through 115 corresponds to a part of the arbitrarily assigned 5' end flanking cotton genomic DNA sequence; positions 116 through 170 correspond to a T-DNA right border (RB) initiation sequence, and positions 171 through 619 correspond to a 7S transcriptional termination sequence (3' to 5'); and positions 620 through 2956 correspond to a 2395 nucleotide sequence of the 3' portion of the Cry1Ac coding region (3' to 5') Nucleotides from position 2957 through 3213 correspond to a 256 nucleotide fragment of the e35S promoter (5' to 3') which is associated with and oriented towards the first 1111 nucleotides of a partial sequence derived from the 5' end coding sequence (5' to 3') for Cry1Ac from positions 3214 through 4326. The arbitrarily assigned 5' end of the functional full length inserted DNA sequence which encodes the full length Cry1Ac protein produced in cotton event 757 follows next, beginning at nucleotide position 4327. Nucleotide position 4327 through 4391 correspond to the T-DNA right border region sequence at the 3' end of the cassette encoding Cry1Ac as set forth in plasmid PV-GHBK04 (FIG. 1), and nucleotides from position 4392 through 4832 correspond to the 7S 3' end transcriptional termination element sequence at the 3' end of the Cry1Ac coding sequence in the full length functional insert portion of the inserted DNA in cotton event 757. Nucleotides from position 4833 through 4973 of SEQ ID NO: 15 correspond to the carboxy terminal amino acid coding sequence for the full length Cry1Ac produced from the full length functional inserted DNA sequence in cotton event 757. The arrangement of all of these genetic elements is contiguous with one another and with the right border region of the functional portion of the insert.

It will be understood by those skilled in the art that, without departing from the scope and spirit of the present invention and without undue experimentation, the present invention can be performed within a wide range of equivalent parameters. While the present invention has been described in connection with specific embodiments thereof, it will be understood that it is capable of further modifications. The present invention covers any uses, variations, or adaptations of the invention following the principles of the invention in general. Various permutations and combination of the elements provided in all the claims that follow are possible and fall within the scope of this invention.

All publications and published patent documents cited in this specification are incorporated herein by reference to the same extent as if each individual publication or patent application was specifically and individually indicated to be incorporated by reference.

What is claimed is:

1. A method of detecting the presence of cotton plant event 757 nucleic acid sequences in a sample comprising the steps of:
   a) contacting said sample with a first nucleotide and a second nucleotide primer sequence which function together in the presence of template cotton plant event 757 nucleic acid sequences to produce an amplicon diagnostic for the cotton plant event 757;
   b) performing a nucleic acid amplification reaction, thereby producing said amplicon; and
   c) detecting said amplicon,
wherein said amplicon comprises SEQ ID NO:2.

2. The method of claim 1 wherein said amplicon comprises a nucleotide sequence comprising at least 11 consecutive nucleotides as set forth in SEQ ID NO: 2.

3. A method of detecting nucleic acid sequence in a sample comprising
   a) contacting the sample with a polynucleotide probe sequence that binds under stringent conditions with said nucleic acid sequence;
   b) subjecting the sample and probe to said stringent conditions; and
   c) detecting the binding of the probe to said nucleic acid sequences,
wherein said probe sequence comprises at least 11 consecutive nucleotides as set forth in SEQ ID NO:2 and said sample comprises a cotton plant event 757 nucleic acid comprising SEQ ID NO: 2.

4. A method of detecting the presence of a DNA molecule in a sample, the method comprising:
   a) contacting the sample with a probe that does not bind under stringent hybridization conditions with DNA from a cotton plant other than cotton plant event 757;
   b) subjecting the probe and sample to stringent hybridization conditions; and
   c) detecting the binding of the probe to said DNA molecule, wherein said sample comprises at least 11 consecutive nucleotides as set forth in SEQ ID NO: 2, and said sample comprises a cotton plant event 757 DNA molecule comprising SEQ ID NO: 2.

5. A method of determining the zygosity of a cotton plant genome comprising SEQ ID NO: 2, said method comprising the steps of:
   a) contacting a sample comprising DNA obtained from said cotton plant with a first and a second nucleotide primer sequence that, when used together in a nucleic acid amplification reaction with a first template comprising cotton plant event 757 DNA, produces a first amplicon that is diagnostic for cotton plant event 757 DNA;

b) performing a nucleic acid amplification reaction with said first and second nucleotide primer sequences and said first template, thereby producing said first amplicon; and c) detecting said first amplicon;

wherein said first amplicon comprises SEQ ID NO:2; and d) contacting said sample with a first and a third nucleotide primer sequence that, when used together in a nucleic acid amplification reaction with a second template comprising cotton plant DNA other than event 757 DNA, produces a second amplicon that is diagnostic for rattan plant DNA other than cotton plant event 757 DNA;

e) performing a nucleic acid amplification reaction with said first and third nucleotide primer sequences and said second template, thereby producing said second amplicon; and f) detecting said second amplicon, wherein detection of said second amplicon is diagnostic for the zygosity of said cotton plant genome.

6. A method for detecting cotton plant event 757 DNA in a biological sample, said plant comprising an inserted heterologous DNA sequence, said method comprising subjecting said sample to a nucleic acid amplification reaction using a primer pair, said primer pair comprising a first primer that is or is complementary to a sequence that is in the genome of said plant and is adjacent to one end of said inserted heterologous DNA sequence, and a second primer that is or is complementary to said inserted heterologous DNA sequence, wherein said reaction produces an amplicon comprising SEQ ID NO:2 that is diagnostic for said plant event DNA in said sample, and detecting said amplicon, and wherein said inserted heterologous DNA sequence comprises SEQ ID NO:14 from nucleotide position 1–206; and said sequence that is in the genome of said plant comprises the complement of SEQ ID NO: 14 from nucleotide position 207–513.

* * * * *